US005811266A

United States Patent [19]
Newgard

[11] Patent Number: 5,811,266
[45] Date of Patent: *Sep. 22, 1998

[54] METHODS FOR PRODUCING HUMAN INSULIN

[75] Inventor: Christopher B. Newgard, Dallas, Tex.

[73] Assignee: Board of Regents, The University of Texas System, Austin, Tex.

[ * ] Notice: The term of this patent shall not extend beyond the expiration date of Pat. No. 5,744,327.

[21] Appl. No.: 312,120

[22] Filed: Sep. 26, 1994

Related U.S. Application Data

[60] Division of Ser. No. 162,044, filed as PCT/US92/04737, Jun. 20, 1992, and a continuation-in-part of Ser. No. 819,326, Jan. 13, 1992, Pat. No. 5,427,940, which is a continuation-in-part of Ser. No. 710,038, Jun. 3, 1991, abandoned, which is a continuation-in-part of Ser. No. 483,224, Feb. 20, 1990, Pat. No. 5,175,085.

[51] Int. Cl.$^6$ ............................. C12N 15/17; C12P 21/02
[52] U.S. Cl. ....................... 435/69.4; 435/69.1; 435/70.1; 435/70.3; 530/303
[58] Field of Search ................................ 435/69.4, 69.1, 435/240.2, 320.1, 71.1, 71.2, 325; 530/350, 303

[56] References Cited

U.S. PATENT DOCUMENTS

| | | |
|---|---|---|
| 4,195,125 | 3/1980 | Wacker . |
| 5,073,491 | 12/1991 | Fanilletti . |
| 5,175,085 | 12/1992 | Johnson et al. ......................... 435/7.21 |
| 5,427,940 | 6/1995 | Newgard . |

FOREIGN PATENT DOCUMENTS

| | | |
|---|---|---|
| 0247494 A2 | 12/1987 | European Pat. Off. . |
| 0334687 | of 1989 | European Pat. Off. . |
| 0383129 | of 1990 | European Pat. Off. . |
| WO 87/05929 | 10/1987 | WIPO . |
| WO 91/09939 | 7/1991 | WIPO . |
| WO 95/05452 | 2/1995 | WIPO . |
| WO 95/09231 | 4/1995 | WIPO . |

OTHER PUBLICATIONS

Aaen et al., "Dependence of Antigen Expression on Functional State of β–Cells," *Diabetes*, 39:697–701, 1990.

Andersson et al., "Effects of Glucose on the Ultrastructure and Insulin Biosynthesis of Isolated Mouse Pancreatic Islets Maintained in Tissue Culture," *Diabetologia*, 10:743–753, 1974.

Arguad et al., "Adenovirus–mediated overexpression of liver 6–phosphofructo–2–kinase/ fructose–2,6–bisphosphatase in gluconeogenic rat hepatoma cells," *J. Biol. Chem.*, 270:24229–24236, 1995.

Asfari et al., "Establishment of 2–Mercaptoethanol–Dependent Differentiated Insulin–Secreting Cell Lines," *Endocrinology*, 130(1):167–178, 1992.

Atkinson et al., "Insulitis and Diabetes in NOD Mice Reduced by Prophylactic Insulin Therapy," *Diabetes*, 39:933–937, 1990.

Becker et al., "Use of recombinant adenovirus for metabolic engineering of mammalian cells," *Methods in Cell Biology*, Roth, M., Ed. New York, Academic Press, 43:161–189, 1994.

Becker et al., "Overexpression of Hexokinase I in Isolated Islets of Langerhans via Recombinant Adenovirus," *J. Biol. Chem.*, 269(33):21234–21238, Aug., 1994.

BeltrandelRio et al., "Molecular on Chemical Reduction in Hexokinase Expression Alters Glucose Dose–Response in Engineered Insulinoma Cells," *Diabetes 43*, Suppl. 1:91A, 1994.

BeltrandelRio et al., "Genetic engineering of insulin secreting cells lines," In *Pancreatic Islet Transplantation vol. 1: Procurement of Pancreatic Islets*, Lanza, R.P. and Chick, W.L. Eds., R.G. Landes Co., 15:169–183, 1994.

Blásquez et al., "Trehalose–6–phosphate, a new regulator of yeast glycolysis that inhibits hexokinases," *FEBS Lett.*, 329(1,2):51–54, Aug., 1993.

Cassidy and Newgard, Glucose–stimulated insulin secretion in cell lines, *Diab. Nutr. Metab.*, 7:189–195, 1994.

Chavez et al., "Expression of exogenous proteins in cells with regulated secretory pathways," *Methods in Cell Biology*, 43 PartA:263–288, 1994.

Chen et al., "Regulated Secretion of Prolactin by the mouse cell line Beta TC–3," *Biotechnology*, 13:1191–1197, 1995.

Clark et al., "Modulation of Glucose–Induced Insulin Secretion from a Rat Clonal β–Cell Line," *Endocrinology*, 127(6):2779–2788, 1990.

Courchesne–Smith et al., "Cytoplasmic Accumulation of a Normally Mitochondrial Malonyl–CoA Decarboxylase by the Use of an Alternate Transcription Start Site," *Arch. Biochem. and Biophys.*, 298(2):576–586, Nov., 1992.

Ferber et al., "Heterogeneity of expression and secretion of native and mutant [Asp B10] insulin in AtT–20 cells," *Mol. Endocrinology*, 5:319–326, 1991.

Ferber et al., "GLUT–2 Gene Transfer into Insulinoma Cells Confers Both Low and High Affinity Glucose–stimulated Insulin Release," *J. Biol. Chem.*, 269(15):11523–11529, Apr., 1994.

(List continued on next page.)

Primary Examiner—Paula K. Hutzell
Assistant Examiner—Stephen Gucker
Attorney, Agent, or Firm—Arnold, White & Durkee

[57] ABSTRACT

The present disclosure relates to the application of genetic engineering to provide artificial β cells, i.e. cells which can secrete insulin in response to glucose. This is achieved preferably through the introduction of one or more genes selected from the insulin gene, glucokinase gene, and glucose transporter gene, so as to provide an engineered cell having all three of these genes in a biologically functional and responsive configuration. Assays for detecting the presence of diabetes-associated antibodies in biological samples using these and other engineered cells expressing diabetes-associated epitopes are described. Also disclosed are methods for the large-scale production of insulin by perfusing artificial β cells, grown in liquid culture, with glucose-containing buffers.

25 Claims, 11 Drawing Sheets

OTHER PUBLICATIONS

Fiedorek et al., "Selective secreting cell lines established from a transplantable rat islet cell tumor," *Mol. Endocrinol.*, 4(7):990–999, 1990.

Finney et al., "Monoclonal Antibodies Against Rat Brain Hexokinase Effects on Catalytic Function and Binding to the Outer Mitochondrial Membrane," *J. Biol. Chem.*, 259(13):8232–8237, 1984.

Gelb et al., "Targeting of hexokinase 1 to liver the hepatoma mitochondria," *Proc. Natl. Acad. Sci. USA*, 89:202–206, Jan., 1992.

Grampp et al., "Use of regulated secretion in protein production from animal cells: An overview," *Advances in Biochemical Engineering*, 46:35–62, 1992.

Gross et al., "Partial diversion of a mutant proinsulin (B10 aspartic acid) from the regulated to the constitutive secretory pathway in transfected AtT–20 cells," *Proc. Natl. Acad. Sci. USA*, 86:4107–4111, 1989.

Gumbiner and Kelly, "Secretory granules of an anterior pituitary cell line, AtT–20, contain only mature forms of corticotropin and beta–lipotropin," *Proc. Natl. Acad. Sci. USA*, 78(1):318–322, Jan., 1981.

Jang et al., "Molecular Cloning, Nucleotide Sequence, and Tissue Distribution of Malonyl–CoA Decarboxylase," *J. Biol. Chem.*, 264(6):3500–3505, Feb., 1989.

Kabir and Wilson, "Mitochondrial Hexokinase in Brain of Various Species: Differences in Sensitivity to Solubilization by Glucose 6–Phosphate," *Arch. Biochem. Biophys.*, 300:641–650, 1993.

Kabir and Wilson, "Mitochondrial Hexokinase in Brain: Coexistence of Forms Differing in Sensitivity to Solubilization by Glucose–6–Phosphate on the Same Mitochondria," *Arch. Biochem. Biophys.*, 310(2):410–416, 1994.

Keller et al., "Insulin prophylaxis in individuals at high risk of type I diabetes," *The Lancet*, 341:927–928, Apr., 1993.

Knaack et al., "Clonal Insulinoma Cell Line That Stably Maintains Correct Glucose Responsiveness," *Diabetes*, 43:1413–1417, Dec., 1994.

Lee et al., "β–Cell lipotoxicity in the pathogenesis of non-–insulin–dependent diabetes mellitus of obese rats: Impairment in adipocyte–β–cell relationships," *Proc. Natl. Acad. Sci. USA*, 91:10878–10882, Nov., 1994.

McGarry and Foster, "Regulation of Hepatic Fatty Acid Oxidation and Ketone Body Production," *Ann. Rev. Biochem.*, 49:395–420, 1980.

McGarry, "What if Minkowski Had Been Ageusic? An Alternative Angle on Diabetes," *Science*, 258:766–770, Oct., 1992.

Milburn et al., "Pancreatic β–Cells in Obesity," *J. Biol. Chem.*, 270(3):1295–1299, Jan., 1995.

Moore and Kelly, "Secretory protein targeting in a pituitary cell line: Differential transport of foreign secretory proteins to distinct secretory pathways," *J. Cell Biol.*, 101:1773–1781, 1985.

Muir, et al., "Insulin Immunization of nonobese diabetic mice induces a protective insulitis characterized by diminished intraislet and interferon–gamma transcription," *J. Clin. Invest.*, 95(2);628–34, Feb., 1995.

Newgard et al., "Engineering of glucose–stimulated insulin release in clonal cells. Therapeutic implications," *Diab. Nutr. Metab.*, 5(Suppl. 1):15–20, 1992.

Newgard et al., "Molecular engineering of glucose–regulated insulin secretion," *In Molecular Biology of Diabetes*, Draznin, B. and LeRoith, D. Eds. Humana Press Inc., Totowa, N.J., Part 1, Chap. 6:1191–54, 1994.

Newgard and McGarry, "Metabolic coupling factors in pancreatic Beta–cell signal transduction," *Ann. Rev. Biochem.*, 64:689–719, 1995.

Newgard, "Perspectives in Diabetes: Cellular Engineering and Gene Therapy Strategies for Insulin Replacement in Diabetes," *Diabetes*, 43:341–350, Mar., 1994.

Newgard et al., "Molecular Engineering of the Pancreatic β–Cell," *J. Lab. Clin. Med.*, 122:356–363, 1993.

Ogawa et al., "Loss of glucose–induced secretion and GLUT2 expression in transplanted β–cells," *Diabetes*, 44:75–79, Jan., 1995.

Polakis and Wilson, "An Intact Hydrophobic N–Terminal Sequence Is Critical for Binding of Rat Brain Hexokinase to Mitochondria," *Arch. Biochem. Biophys.*, 236(1):328–337, Jan., 1985.

Randle et al., "Mechanisms Decreasing Glucose Oxidation in Diabetes and Starvation: Role of Lipid Fuels and Hormones," *Diabetes, Metab. Rev.*, 4(7):623–638, 1988.

Sambanis et al., "Multiple episodes of induced secretion of human growth hormone from recombinant AtT–20 cells," *Cytotechnology*, 4:111–119, 1990.

Sambanis et al., "Use of regulated secretion in protein production from animal cells: An evaluation with the AtT–20 model cell line," *Biotechnology and Bioengineering*, 35:771–780, 1990.

Sambanis et al., "A model of secretory protein trafficking in recombinant AtT–20 cells," *Biotechnology and Bioengineering*, 36:280–295, 1991.

Scharp et al., "Protection of Encapsulated Human Islets Implanted Without Immunosuppression in Patients With Type I or Type II Diabetes and in Nondiabetic Control Subjects," *Diabetes*, 43:1167–1170, Sep., 1994.

Schmidt and Moore, "Synthesis and targeting of insulin–like growth factor–1 to the hormone storage granules in an endocrine cell line," *J.B.C.*, 269:27115–27124, 1994.

Schnedl et al., "STZ Transport and Cytotoxicity," *Diabetes*, 43:1326–1333, Nov., 1994.

Takeda et al., "Organization of the Human GLUT2 (Pancreatic β–Cell and Hepatocyte) Glucose Transporter Gene," *Diabetes*, 42:773–777, May, 1993.

Ting and Lee, "Human Gene Encoding the 78,000–Dalton Glucose–Regulated Protein and Its Pseudogene: Structure, Conservation, and Regulation," *DNA*, 7(4):275–286, 1988.

Chen et al., "Regulation of β–cell glucose transporter gene expression," Proc. Natl. Acad. Sci., 87:4088–4092, 1990.

Shibasaki et al., "Overexpression of glucose transporter modulates insulin biosynthesis in insulin producing cell line," FEBS Lett., 270 (1,2):105–107, 1990.

Johnson et al., "Underexpression of β Cell High Km Glucose Transporters in Noninsulin–Dependent Diabetes," Science, 250:546–549, 1990.

Orci et al., "Evidence that down–regulation of β–cell glucose transporters in non–insulin–dependent diabetes may be the cause of diabetic hyperglycemia," Proc. Natl. Acad. Sci., 87:9953–9957, 1990.

Johnson et al., "The High Km Glucose Transporter of Islets of Langerhans Is Functionally Similar to the Low Affinity Transporter of Liver and Has an Identical Primary Sequence," J. Biol. Chem., 265(12):6548–6551, 1990.

Newgard et al., "Glucokinase and glucose transporter expression in liver and islets: implications for control of glucose homeostasis," Biochem. Soc. Trans., 18:851–853, 1990.

Newgard et al., "Analysis of glucokinase and glucose transporter gene products in islet, liver, and anterior pituitary cells and their role in glucose sensing," FASEB J. 4(7) :A2008, Abstract # 1827.

Matsutani et al., "Polymorphisms of GLUT2 and GLUT4 Genes," Diabetes, 39:1534–1542, 1990.

Bakkeskov et al., "Antibodies to a 64,000 $M_r$ Human Islet Cell Antigen Precede the Clinical Onset of Insulin–dependent Diabetes," J. Clin. Invest., 79:926–934, 1987.

Bakkeskov et al., "Identification of the 64K autoantigen in insulin–dependent diabetes as the GABA–synthesizing enzyme glutamic acid decarboxylase," Nature, 347:151–156, 1990.

Kaufman et al., "Brain Glutamate Decarboxylase Cloned in Agt–11: Fusion Protein Produces γ–Aminobutyric Acid," Science, 232:1138–1140, 1986.

Johnson et al., "Inhibition of glucose transport into rat islet cells by immunoglobulins from patients with new–onset insulin–dependent diabetes mellitus," N. Engl. J. Med., 322(10) :653–659.

Permutt et al., "Cloning and functional expression of a human pancreatic islet glucose–transporter cDNA," Proc. Natl. Acad. Sci., 86:8688–8692, 1989.

Iynedjian et al., "Differential expression and regulation of the glucokinase gene in liver and islets of Langerhans," Proc. Natl. Acad. Sci., 86:7838–7842, 1989.

Maclaren, N.K., "Perspectives in Diabetes: How, When, and Why to Predict IDDM," Diabetes, 37:1591–1593, 1988.

Thorens et al., "Cloning and Functional Expression in Bacteria of a Novel Glucose Transporter Present in Liver, Intestine, Kidney and β–Pancreatic Islet Cells," Cell, 55:281–290, 1988.

Selden et al., "Regulation of insulin–gene expression: Implications for gene therapy," N. Engl. J. Med., 317(17):1067–1076, 1987.

Kuwajima et al., "The glucose–phosphorylating capacity of liver as measured by three independent assays," J. Biol. Chem., 261(19):8849–8853, 1986.

Eisenbarth, G.S., "Type I Diabetes Mellitus: A Chronic Autoimmune Disease," N. Engl. J. Med., 314(21) :1360–1368, 1986.

Mueckler et al., "Sequence and structure of a human glucose transporter," Science, 229:941–945, 1985.

Kanatsuna et al., "Immunoglobulin from insulin–dependent diabetic childrens inhibits glucose–induced insulin release," Diabetes, 32:520–523, 1983.

Whitesell et al., "Transport and Metabolism of Glucose in an Insulin–Secreting Cell Line, βTC–1," Biochemistry (1991) 30 (49):11560–11566. Published in USA.

Tal et al., "Glucose Transporter Isotypes Switch in T–Antigen–Transformed Pancreatic β Cells Growing in Culture and in Mice," Mol. Cell. Biol. (Jan. 1992) 12(1):422–432. Published in USA.

Lacy et al., "Maintenance of Normoglycemia in Diabetic Mice by Subcutaneous Xenografts of Encapsulated Islets," Science (Dec. 20, 1991) 254:1782–1784. Published in USA.

Sullivan et al., "Biohybrid Artificial Pancreas: Long–Term Implantation Studies in Diabetic, Pancreatectomized Dogs," Science (May 3, 1991) 252:718–721. Published in USA.

Hughes et al., "Engineering of Glucose–Stimulated Insulin Secretion and Biosynthesis in Non–Islet Cells," Proc. Natl. Acad. Sci. USA (Jan. 1992) 89:688–692. Published in USA.

Hughes et al., "Expression of Normal and Novel Glucokinase mRNAS in Anterior Pituitary and Islet Cells," J. Biol. Chem. (Mar. 5, 1991) 266(7):4521–4530. Published in USA.

Berson et al., "Insulin–$I^{131}$ Metabolism in Human Subjects: Demonstration of Insulin Binding Globulin in the Circulation of Insulin Treated Subjected," J. Clin. Invest., 35:170–190, 1956.

Bottazzo et al., "Islet–Cell Antibodies in Diabetes Mellitus with Autoimmune Polyendocrine Deficiencies," Lancet, 7884(II), 1279–1283, 1974.

Christie, Michael R. et al., "Cellular and Subcellular Localization of an $M_r$ 64,000 Protein Autoantigen in Insulin–Dependent Diabetes," J. Biol. Chem., 265(1):376–381, 1990.

Flier, Jeffrey S. et al., "Distribution of Glucose Transporter Messenger RNA Transcripts in Tissues of Rat and Man," J. Clin. Invest., 79:926–934, 1987.

Hellman et al., "Evidence for Mediated Transport of Glucose in Mammalian Pancreatic β–Cells," Biochem. Biophys. Acta, 241:147–154, 1971.

Johnson, J. et al., "Inhibition or Rat Islet 3–0–Methyl–D––Glucose (30MG) Uptake by Serum of Rats and Humans with Autoimmune Diabetes," Annual Meeting Program Published in Diabetes, 1987.

Kanatsuna et al., "Block in Insulin Release from Column––Perifused Pancreatic β–Cells Induced by Islet Cell Surface Antibodies and Complement," Diabetes 30(1):231–234, 1981.

Leary, "Researchers Closing In On a Large–Scale Test to Screen for Diabetes," New York Times, 19 Jun. 1990.

Lernmark, A., and S. Baekkeskov, "Islet Cell Antibodies––Theoretical and Practical Implications," Diabetologia, 21:431–435, 1981.

Maclaren, Noel Keith, and Shih–Wen Huang, "Antibody to Cultured Human Insulinoma Cells in Insulin–Dependent Diabetes," Lancet, 997–999, 1975.

Pozzilli, O. et al., "Monocional Antibodies Defined Abnormalities of T–Lymphocytes in Type I (Insulin–Dependent) Diabetes," Diabetes, 32:91–93, 1983.

Rubin, "Research May Aid Diabetics," Dallas Morning Herald, 8 Mar., 1990.

Tominaga, Makoto et al., "Loss of Insulin Response to Glucose but Not Arginine During the Development of Autoimmune Diabetes in BB/W Rats: Relationships to Islet Volume an Glucose Transport Rate," Proc. Natl. Acad. Sci. USA, 83:9749–9753, 1986.

Rapoport et al., "Synthesis of Carp Proinsulin in Xenopus Oocytes," Eur. J. Biochem., 87:229–233, 1978.

Yip et al., "Translation of Messenger Ribonucleic Acid from Isolated Pancreatic Islets and Human Insulinomas," Proc. Natl. Acad. Sci. USA, 72:4777–4779, 1975.

Chen et al., "Recovery of Glucose–Induced Insulin Secretion in a Rat Model of NIDDM is Not Accompanied by Return of the B–Cell GLUT2 Glucose Transporter," Diabetes, 41:1320–1327, 1992.

MacDonald, Michael J., "Elusive Proximal Signals of β–Cells for Insulin Secretion," Diabetes, 39:1461–1466, 1990.

Miyazaki et al., "Establishment of a Pancreatic β Cell Line That Retains Glucose–Inducible Insulin Secretion: Special Reference to Expression of Glucose Transporter Isoforms," Endocrinology, 127(1):126–132, 1990.

Rasschaert et al., "Long Term in Vitro Effects of Streptozotocin, Interleukin–1 and High Glucose Concentration on the Activity of Mitochondrial Dehydrogenases and the Secretion of Insulin in Pancreatic Islets," *Endocrinology*, 130(5):3522–3528, 1992.

Tal et al., "[Val$^{12}$] HRAS Downregulates GLUT2 in β Cells of Transgenic Mice without Affecting Glucose Homeostasis," *Proc. Natl. Acad. Sci. USA*, 89:5744–5748, 1992.

Prentki et al., "Malonyl–CoA and Long Chain Acyl–CoA Esters as Metabolic Coupling Factors in Nutrient–Induced Insulin Secretion," *J. Biol. Chem.*, 267(9):5802–5810, 1992.

MacDonald et al., "Pyruvate Dehydrogenase and Pyruvate Carboxylase," *J. Biol. Chem.*, 266(33):22392–22397, 1991.

Hughes et al., "Transfection of AtT–20$_{ins}$ Cells with GLUT–2 but Not GLUT–1 Confers Glucose–Stimulated Insulin Secretion," *J. Biol. Chem.*, 268(20):15205–15212, 1993.

Asano et al., "Rabbit Brain Glucose Transporter Responds to Insulin When Expressed in Insulin–Sensitive Chinese Hamster Ovary Cells," *J. Biol. Chem.*, 264(6):3416–3420, 1989.

Capecchi, Mario R., "Altering the Genome by Homologous Recombination," *Science*, 244:1288–1292, 1989.

Bell et al., "Molecular Biology of Mammalian Glucose Transporters," *Diabetes Care*, 13(3):198–208, 1990.

Weinhouse et al., "Regulation of Glucokinase in Liver," *Current Topics in Cellular Regulation*, 11:1–50, 1976.

Efrat, Shimon et al., "Beta–Cell Lines Derived from Transgenic Mice Expressing a Hybrid Insulin Gene–Oncogene," *Proc. Natl. Acad. Sci. USA*, 85:9037–9041, 1988.

Becker, et al., "Use of Recombinant Adenovirus Vectors for High–Efficiency Gene Transfer into the Islets of Langerhans," abstract No. 29, *Diabetes*, Abstract book, 53rd Annual Meeting, Jun. 12–15, 1993, Las Vegas, NV.

Ferber, et al., "Molecular Strategies for the Treatment of Diabetes," *Transplant, Proc.*, 26(2):363–365 (Apr. 1994).

Mastrangeli, et al., "Diversity of Airway Epithelial Cell Targets for In Vivo Recombinant Adenovirus–mediated Gene Transfer," *J. Clin. Invest.*, 91(1):225–234 (1993).

Newgard, C., "Cellular Engineering for the Treatment of Metabolic Disorders: Prospects for Therapy in Diabetes," *Biotechnology*, 10:1112–1120 (Oct. 1992).

Newgard, et al., "Molecular engineering of the pancreatic β–cell," *J. Labor. Clin. Med.*, 122(4):356–363 (1993).

Shih, et al., "An Adenoviral Vector System for Functional Indentification of Nuclear Receptor Ligands," *Mol. Endo.*, 5(2):300–309 (1991).

Harrison et al., Insulin Action on Activity and Cell Surface Disposition of Human HepG2 Glucose Transporters Expressed in Chinese Hamster Ovary Cells, *The Journal of Biological Chemistry*, 265(10):5793–5801, 1990.

Iynedjian et al., "Molecular Cloning of Glucokinase cDNA," *J. Biol. Chem.*, 252:6032–6038, 1987.

Magnuson and Shelton, "An Alternate Promoter in the Glucokinase Gene Is Active in the Pancreatic β Cell," *J. Biol. Chem.*, 264:15936–15942, 1989.

Shimizu et al., "Control of Glucose Metabolism in Pancreatic β–Cells by Glucokinase, Hexokinase, and Phosphofructokinase," *Diabetes*, 37:1524–1530, 1988.

Santerre et al., *PNAS, USA*, vol. 78, pp. 4339–4343, 1981.

Moore et al., *Cell*, vol. 35, pp. 531–538, 1983.

Cullen et al., *Endocrinology*, vol. 125, pp. 1774–1782, 1989.

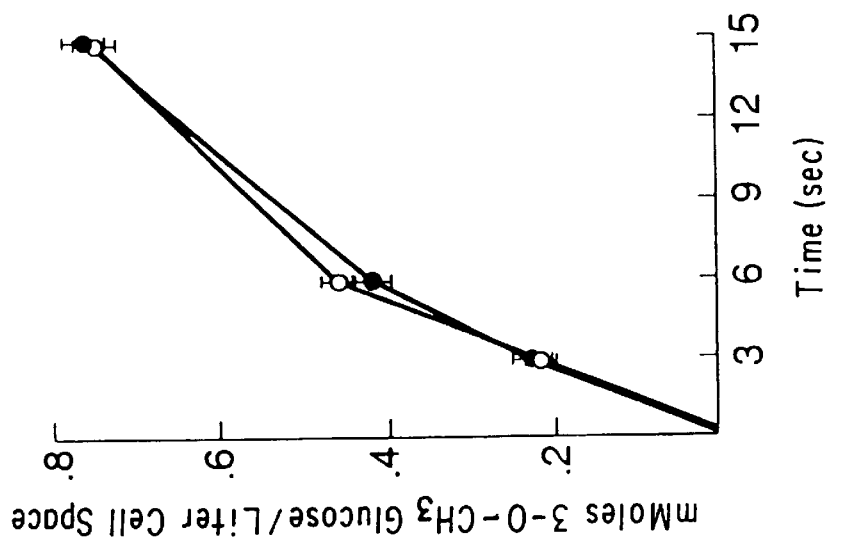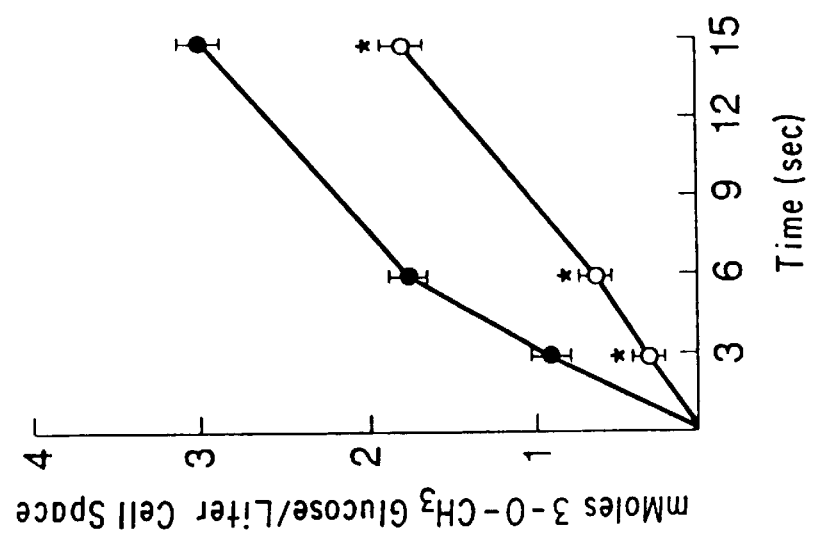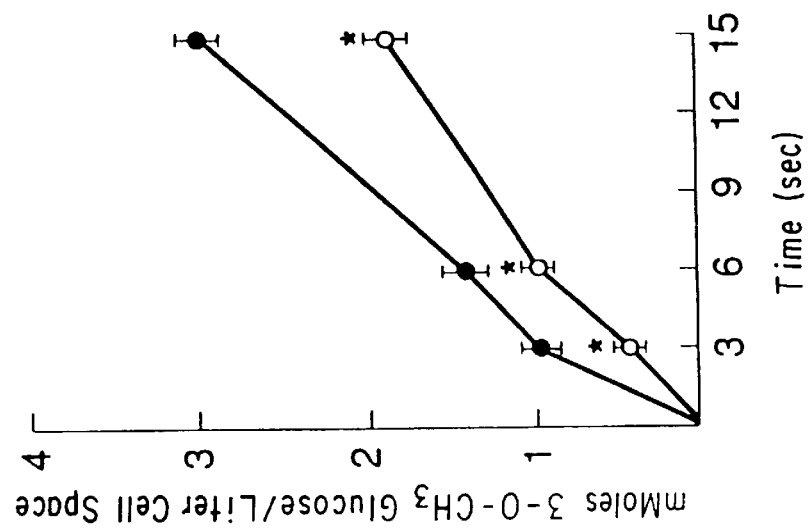

SEQUENCE LISTING ( 1 ) GENERAL INFORMATION:

( i i i ) NUMBER OF SEQUENCES: 1

(2) INFORMATION FOR SEQ ID NO:1:

(i) SEQUENCE CHARACTERISTICS:
        (A) LENGTH: 14 amino acids
        (B) TYPE: amino acid
        (C) STRANDEDNESS: single
        (D) TOPOLOGY: linear (xi) SEQUENCE DESCRIPTION: SEQ ID NO:1:

| Asp | Ala | Trp | Glu | Glu | Glu | Thr | Glu | Gly | Ser | Ala | His | Ile | Val |
|---|---|---|---|---|---|---|---|---|---|---|---|---|---|
| 1 | | | | 5 | | | | | 10 | | | | |

METHODS FOR PRODUCING HUMAN INSULIN

The present application is a division of U.S. Ser. No. 08/162,044, filed Jun. 23, 1994, which was a United States nationalization of PCT US92/04737, filed Jun. 2, 1992, and a continuation-in-part of U.S. Ser. No. 07/819,326, filed Jan. 13, 1992 now U.S. Pat. No. 5,427,940, which was a continuation in part of U.S. Ser. No. 07/710,038, filed Jun. 3, 1991, now abandoned; and further includes subject matter that constitutes a continuation-in-part of U.S. Ser. No. 07/483,224, filed Feb. 20, 1990 now U.S. Pat. No. 5,175,085; the disclosures of which are incorporated herein by reference.

FIELD OF THE INVENTION

The present invention relates generally to the preparation, culture and use of engineered cells having the ability to secrete insulin in response to glucose, to methods for the detection of diabetes-associated antigens, and to methods employing engineered cells in the production of human insulin for use in, for example, type I diabetes mellitus. In particular aspects, the present invention relates to the growth of engineered cells in liquid culture and the increase in glucose-mediated insulin release by such cells.

DESCRIPTION OF THE RELATED ART

Insulin-dependent diabetes mellitus (IDDM, also known as Juvenile-onset, or Type I diabetes) represents approximately 15% of all human diabetes. IDDM is distinct from non-insulin dependent diabetes (NIDDM) in that only IDDM involves specific destruction of the insulin producing β-cells of the islets of Langerhans in the pancreas. The destruction of β-cells in IDDM appears to be a result of specific autoimmune attack, in which the patient's own immune system recognizes and destroys the β-cells, but not the surrounding α (glucagon producing) or δ (somatostatin producing) cells that comprise the islet.

The precise events involved in β-cell recognition and destruction in IDDM are currently unknown, but involve both the "cellular" and "humoral" components of the immune system. In IDDM, islet β-cell destruction is ultimately the result of cellular mechanisms, in which "killer T-cells" destroy β cells which are erroneously perceived as foreign or harmful. The humoral component of the immune system, comprised of the antibody-producing B cells, is also inappropriately active in IDDM patients, who have serum antibodies against various β cell proteins. Antibodies directed against intracellular proteins probably arise as a consequence of β-cell damage which releases proteins previously "unseen" by the immune system. However, the appearance of antibodies against several cell surface epitopes such as insulin, proinsulin, the "38 kD protein", immunoglobulins, the 65 kD heat shock protein and the 64 kD and 67 kD forms of glutamic acid decarboxylase (GABA) are believed to be linked to the onset of IDDM (Lernmark, 1982). Antibodies in diabetic sera may also interact with the islet GLUT-2 glucose transporter (Johnson, et al., 1990c).

A progressive loss of β-cell function is observed in the early stages of NIDDM and IDDM, even prior to the autoimmune β cell destruction in IDDM. The specific function of glucose-stimulated insulin release is lost in islets of diabetic patients, despite the fact that such islets continue to respond to non-glucose secretagogues such as amino acids and isoproterenol (Srikanta, et al., 1983).

The participation of the pancreatic islets of Langerhans in fuel homeostasis is mediated in large part by their ability to respond to changes in circulating levels of key metabolic fuels by secreting peptide hormones. Accordingly, insulin secretion from islet β-cells is stimulated by amino acids, three-carbon sugars such as glyceraldehyde, and most prominently, by glucose. The capacity of normal islet β-cells to "sense" a rise in blood glucose concentration, and to respond to elevated levels of glucose (as occurs following ingestion of a carbohydrate containing meal) by secreting insulin is critical to control of blood glucose levels. Increased insulin secretion in response to a glucose load prevents chronic hyperglycemia in normal individuals by stimulating glucose uptake into peripheral tissues, particularly muscle and adipose tissue.

Mature insulin consists of two polypeptide chains, A and B, joined in a specific manner. However, the initial protein product of the insulin gene in β-cells is not insulin, but preproinsulin. This precursor differs from mature insulin in two ways. Firstly, it has a so-called N-terminal "signal" or "pre" sequence which directs the polypeptide to the rough endoplasmic reticulum, where it is proteolytically processed. The product, proinsulin, still contains an additional connecting peptide between the A and B chains, known as the C-peptide, which permits correct folding of the whole molecule. Proinsulin is then transported to the Golgi apparatus, where enzymatic removal of the C-peptide begins. The processing is completed in the so-called secretory granules, which bud off from the Golgi, travel to, and fuse with, the plasma membrane thus releasing the mature hormone.

Glucose stimulates de novo insulin biosynthesis by increasing transcription, MRNA stability, translation, and protein processing. Glucose also rapidly stimulates the release of pre-stored insulin. While glucose and non-glucose secretagogues may ultimately work through a final common pathway involving alterations in $K^+$ and $CA^{++}$ channel activity and increases in intracellular $CA^{++}$ (Prentki, et al., 1987; Turk, et al., 1987), the biochemical events leading from changes in the levels of a particular fuel to insulin secretion are initially diverse. In the case of glucose, transport into the β-cell and metabolism of this sugar are absolute requirements for secretion, leading to the hypothesis that its specific stimulatory effect is mediated by, and proportional to, its flux rate through glycolysis and related pathways (Ashcroft, 1980; Hedeskov, 1980; Meglasson, et al., 1986; Prentki, et al., 1987; Turk, et al. 1987; Malaisse, et al., 1990). Strong support for this view comes from the finding that non-metabolizable analogues of glucose such as 3-O-methyl or 2-deoxy glucose fail to stimulate insulin release (Ashcroft, 1980; Meglasson, et al., 1986).

A substantial body of evidence has accumulated implicating a specific facilitated-diffusion type glucose transporter known as GLUT-2, and the glucose phosphorylating enzyme, glucokinase, in the control of glucose metabolism in islet β-cells. Both proteins are members of gene families; GLUT-2 is unique among the five-member family of glucose transporter proteins in that it has a distinctly higher Km and Vmax for glucose. Glucokinase is the high Km and high Vmax counterpart of GLUT-2 among the family of hexokinases (Weinhouse, 1976). Importantly, both proteins have affinities for glucose that allow dramatic changes in their activities over the physiological range of glucose. This has led to the hypothesis that these proteins work in concert as the "glucose-sensing apparatus" that modulates insulin secretion in response to changes in circulating glucose concentrations by regulating glycolytic flux (Newgard, et al., 1990; Johnson, et al., 1990a).

In normal β-cells, glucose transport capacity is in excess relative to glycolytic flux. Thus, the GLUT-2 transporter likely plays a largely permissive role in the control of glucose metabolism, while glucokinase represents the true rate-limiting step (Meglasson, et al., 1986; Newgard, et al., 1990). Implicit in this formulation, however, is the prediction that severe underexpression of GLUT-2 will result in loss of glucose-stimulated insulin secretion in islets, an idea that has recently received strong experimental support from studies with spontaneous (Johnson, et al., 1990b; Orci, et al., 1990) as well as experimentally induced (Chen, et al., 1990; Thorens, et al., 1990b) animal models of β-cell dysfunction, which have clear similarities to the β-cell impairment observed in human NIDDM. Furthermore, RINm5F clonal insulinoma cells derived from islet β-cells express GLUT-1, a transporter with a substantially lower Km and Vmax for glucose, as their predominant glucose transporter instead of GLUT-2. This may explain the finding that the clonal cells fail to respond to glucose as an insulin secretagogue (Thorens, et al., 1988).

Currently, there are significant deficiencies both in the diagnosis and treatment of diabetes, particularly IDDM. For example, the most common clinical diagnostic test, the oral glucose tolerance test (OGTT) suffers from severe drawbacks, such as subjective interpretation and the ability to only identify individuals with advanced disease. The serological test for cytoplasmic islet cell antibodies (ICA-cyt) (Bright, 1987; Gleichmann et al., 1987) is a diagnostic procedure for detecting the onset of diabetes, which involves binding of patients' antibodies to cryostat sections of fresh human or primate pancreas. One evident disadvantage of this is the requirement for fresh human or primate tissue. Further difficulties are: false negatives (40%); subjective interpretation; poor reproducibility; and the inability to detect cell surface-directed antibodies which are known to specifically damage β cells (Doberson, et al., 1980).

Even less progress has been made in developing new therapeutic strategies for diabetics. Significant effort has been devoted to the strategy of islet or pancreas fragment transplantation as a means for permanent insulin replacement (Lacy, et al., 1986). However, this approach has been severely hampered by the difficulties associated with obtaining tissue, as well as the finding that transplanted islets are recognized and destroyed by the same autoimmune mechanism responsible for destruction of the patients original islet β cells.

Treatment for diabetes is still centered around self-injection of insulin once or twice daily. Both recombinant and non-recombinant methods are currently employed for the industrial production of human insulin for therapeutic use. Recombinant methods generally include the expression of recombinant proinsulin in bacteria or yeast, followed by chemical treatment of the proinsulin to ensure correct disulfide bond linkages between the A and B chains of the mature insulin molecule. The proinsulin produced by microorganisms is processed to insulin by the addition of proteolytic enzymes. Thereafter, the mature insulin peptide must be purified away from the bacterial or yeast proteins, as well from the added proteases. The bacterial procedure involves 40 distinct steps. The non-recombinant methods typically include the purification of pig insulin from freshly isolated porcine pancreas or pancreatic islets. Each of the above methods suffer from the drawbacks of being technically difficult and laborious. The latter method is further complicated by the fact that the pancreas is a complex proteinaceous tissue with high levels of active proteases that can degrade insulin and render it inactive as a hormone.

Accordingly, it is evident that improvements are needed both in the treatment and diagnosis of diabetes and in the methods of insulin production for current therapeutic application.

SUMMARY OF THE INVENTION

The present invention is intended to address such disadvantages present in the prior art. In general, the invention is based on the inventor's discovery that recombinant DNA technology and cell culture methods may be employed to engineer an "artificial β cell" that secretes insulin in response to glucose. The present invention provides a means of preparing artificial β cells that it is proposed can be employed in a variety of applications, such as, e.g., in the detection of diabetes-associated antigens, in the clinical treatment of IDDM and even in the large-scale production of correctly-folded insulin. In further aspects, the current invention provides methods for growing artificial β cells in liquid culture on gelatin beads and for the increased production of human insulin by perifusion of such recombinant cells with glucose-containing buffers.

Turning first to embodiments directed to the recombinant engineering of cells secreting insulin in response to glucose, it should be pointed out that this aspect of the invention relates generally to an engineered cell that includes a gene, preferably a recombinant gene, encoding a functional glucose transporter protein, wherein the engineered cells secrete insulin in response to glucose. This aspect of the invention is based generally on the inventor's finding that where a cell is competent to secrete insulin generally, it may be converted to a glucose-responsive cell through the introduction of a gene encoding a functional glucose transporter protein, such as a GLUT gene. For most purposes leading up to the ultimate treatment of the diabetic condition, one will desire to employ GLUT-2 as the recombinant glucose transporter gene. This is because the GLUT-2 gene corresponds to that found and normally expressed in β cells, and it is believed that this gene will ultimately provide a more physiological response than other types of glucose transporters.

As used herein, the term "engineered" or "recombinant" cell is intended to refer to a cell into which a recombinant gene, such as a gene encoding a functional glucose transporter protein, has been introduced. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a cDNA gene (i.e., they will not contain introns), a copy of a genomic gene, genes produced by synthetic means, and/or genes positioned adjacent to a promoter not naturally associated with the particular introduced gene.

Generally speaking, it will be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude larger than the cDNA gene. However, the inventor does not exclude the possibility of employing a genomic version of a particular gene where desired.

Engineered cells of the present invention will generally be derived from a cell line comprised of cells capable of forming secretory granules. Secretory granules are generally confined to mammalian cells whose main function is the synthesis and secretion of peptides. Generally speaking, secretory granules are found in endocrine cells. Secretory granules are formed by budding of intracellular membranous structures known as the Golgi apparatus. Polypeptide hormones are usually synthesized as prohormones and undergo proteolytic processing to yield the shorter, mature version of the hormone.

Thus, for example, the initial protein product of the insulin gene in β-cells is preproinsulin. This precursor differs from mature insulin in that it has a so-called "signal sequence" at its N-terminus, consisting of a stretch of hydrophobic amino acids that guide the polypeptide to the rough endoplasmic reticulum. It also has a connecting peptide between the A and B chains that comprise the mature insulin molecule; this connector is known as the "C-peptide". The preproinsulin molecule enters the lumen of the endoplasmic reticulum, in the process having its hydrophobic N-terminal "pre" region proteolytically removed. The processed, correctly folded proinsulin molecule (still containing the C-peptide) is then transported to the Golgi apparatus. As the precursor is transported through the Golgi apparatus, enzymatic removal of the C-peptide connector begins.

Secretory granules are derived from Golgi membranes by a process of budding off and eventual separation. The resulting granule envelopes the mixture of unprocessed proinsulin and the small amount of mature insulin. Most of the processing of proinsulin to insulin occurs shortly after formation of the secretory granules by virtue of the fact that the enzymes responsible for this processing are found at highest concentration within the granules. The granules are transported to the plasma membrane surface of the cell in response to secretary stimuli such as glucose; whereupon they fuse with the plasma membrane and release their stores of the mature hormone. The important and unique features of this system are 1) the secretary granules allow a supply of a particular hormone to be built up and stored for release at the time when it is needed to perform its function and 2) the presence of processing enzymes in t he granules allow efficient conversion of the precursor forms of hormones to the mature forms. Cells that lack secretory granules will thus likely not be useful for the purposes of this aspect of the invention.

Therefore, cells used in this aspect will preferably be derived from an endocrine cell, such as a pituitary or thyroid cell. Particularly preferred endocrine cells will be AtT-20 cells, which are derived from ACTH secreting cells of the anterior pituitary gland, GH1 or the closely related GH3 cells, which are derived from growth hormone producing cells of the anterior pituitary, or other cell lines derived from this gland. AtT-20 cells are preferred for the following reasons. First, these cells have been modified for insulin gene expression by stable transfection with a viral promoter/human proinsulin cDNA construct (this derivation of the AtT-20 cell line is known as AtT-20ins; both the parental AtT-20 cell line and the insulin expressing AtT-20ins cell line are available from American Type Culture Collection, 12301 Parklawn Drive, Rockville, Md. 20852). Second, AtT-20ins cells are able to process the proinsulin MRNA and preprotein to yield the correctly processed insulin polypeptide. Third, their insulin secretory response to analogues of cAMP compares favorably with the well-differentiated hamster insulinoma (HIT) cell line which is derived from hamster islet β-cells. Finally, studies from the inventor's laboratory have recently shown that AtT-20ins cells contain significant amounts of the islet isoform of glucokinase, making this the only tissue other than liver or islets in which glucokinase gene expression has been reported.

GH1 and GH3 cells were originally derived from the same batch of cells isolated from a rat pituitary gland tumor. GH3 cells differ from GH1 cells in that they secrete more growth hormone and also secrete prolactin (both lines are available from the American Type Culture Collection). These cells are believed to be preferred for the practice of the invention because it has been shown that introduction of a recombinant preprosomatostatin gene into these cells results in secretion of the mature somatostatin peptide (Stoller, et al., 1989); Processing of the endogenous preprosomatostatin gene also occurs in δ-cells of the islets of Langerhans. The finding that an islet hormone precursor can be correctly processed in growth hormone secreting cells of the anterior pituitary suggests that proinsulin processing will also occur in these cell, perhaps even more efficiently than in AtT-20ins cells.

A number of cell lines derived from β-cells, commonly known as insulinoma cells, are also preferred for the practice of this invention and are readily available, particularly as concerns the therapeutic aspects of the work. For example, hamster insulinoma (HIT-T15) cells are well studied and are readily available from the American Type Tissue Collection. A number of rat insulinoma cell lines are also available. The RINm5F and RINr1046-38 cell lines were derived from a radiation induced tumor of the islet β-cells (Gazdar, et al., 1980; Clark, et al., 1990). MSL-G2 cells were derived from a liver metastasis of an islet cell tumor. These cells require periodic passage in an animal host in order to maintain expression of their endogenous insulin gene (Madsen, et al., 1988). Finally, the β-TC insulinoma cell line has been recently derived from transgenic animals injected with a T-antigen gene driven by an insulin promoter, resulting in specific expression of T-antigen in islet β-cells and consequent immortalization of these cells (Efrat, et al., 1988).

RIN 1046-38 cells have been shown in the inventor's laboratory to express both GLUT-2 and glucokinase (Hughes, et al., 1991), and have been shown by Clark, et al. (1990) to be responsive to glucose. Glucose stimulation of insulin release from these cells is maximal at 0.5 mM glucose, however, a level far below the stimulatory concentration of glucose required for insulin release from normal β-cells. Recent studies in the inventor's laboratory have shown that this hypersensitivity to glucose in RIN 1046-38 cells may be due to high levels of hexokinase activity. Hexokinase performs the same function as glucokinase (glucose phosphorylation) but does so at much lower glucose concentrations (hexokinase has a Km for glucose of approximately 0.05 mM versus 8 mM for glucokinase). It is proposed that lowering of hexokinase activity by methods of recombinant DNA technology described below might make RIN cells useful for the practice of this invention.

Of course, the type of engineering that will be required in order to achieve a cell that secretes insulin in response to glucose will depend on the property of the starting cell. In general, the inventor proposes that in addition to the ability to form secretry granules, th e ability to functionally express certain genes is important. The functional genes that are required include an insulin gene, a glucose transporter gene and a glucokinase gene. In the practice of the invention, one or more of these genes will be a recombinant gene. Thus, if the starting cell has a functional insulin gene and a functional glucokinase gene, and these genes are expressed at levels similar to their expression in β-cells, but the cell does not have a functional glucose transporter gene, introduction of a recombinant glucose transporter gene will be required.

Conversely, if the starting cell expresses none of the aforementioned genes in a functional fashion, or at physiologic levels, it will be necessary to introduce all three. Since recombinant versions of all three categories of genes are available to the art, and the specific technology for in producing such genes into cells is generally known, the construction of such cells will be well within skill of the art in light of the specific disclosure herein.

As stated above, particularly preferred endocrine cells for use in accordance with the present invention are AtT-20$_{ins}$ cells, which have been stably transfected to allow the production of correctly processed human insulin. Also as stated, it is generally preferred to employ the GLUT-2 isozyme to provide recombinant cells with a functional glucose transporter. Engineered cells that combine both of these features have been created by the inventor, and one form of cell expressing high levels of GLUT-2 mRNA, termed CTG-6 cells, are envisione d by the inventor to be of particular use in aspects of the present invention.

Where the introduction of a recombinant version of one or more of the foregoing genes is required, it will be important to introduce the gene such that it is under the control of a promoter that effectively directs the expression of the gene in the cell type chosen for engineering. In general, one will desire to employ a promoter that allows constitutive (constant) expression of the gene of interest. Commonly used constitutive promoters are generally viral in origin, and include the cytomegalovirus (CMV) promoter, the Rous sarcoma long-terminal repeat (LTR) sequence, and the SV40 early gene promoter. The use of these constitutive promoters will ensure a high, constant level of expression of the introduced genes. The inventor has noticed that the level of expression from the introduced gene(s) of interest can vary in different clones, probably as a function of the site of insertion of the recombinant gene in the chromosomal DNA. Thus, the level of expression of a particular recombinant gene can be chosen by evaluating different clones derived from each transfection experiment; once that line is chosen, the constitutive promoter ensures that the desired level of expression is permanently maintained. It may also be possible to use promoters that are specific for cell type used for engineering, such as the insulin promoter in insulinoma cell lines, or the prolactin or growth hormone promoters in anterior pituitary cell lines.

Certain particular embodiments of the invention are directed to engineering cells with reduced hexokinase activity relative to the cell line from which it was prepared. There are four known isoforms of hexokinase in mammals. Hexokinases I, II, and III have very low Kms (high affinities) for glucose, on the order of 0.05 mM. Hexokinase IV is glucokinase, which has a high Km for glucose of around 8–10 mM. In the islet β-cell, glucokinase is the predominant glucose phosphorylating enzyme, while in most clonal cell lines grown in culture, the low Km hexokinase I isoform predominates. The inventor proposes that expression of hexokinases other than glucokinase at high levels in clonal cells used for engineering will tend to make the cell glucose-responsive in terms of insulin release at lower concentrations of glucose than is desirable. Thus, it is proposed that the lower the hexokinase/glucokinase ratio, the more physiologic the insulin response.

Various approaches may be taken to reduce the hexokinase activity in engineered cells. One approach involves the introduction of an antisense RNA molecule. Antisense RNA technology is now fairly well established, and involves the juxtaposition of the targeted gene in a reverse orientation behind a suitable promoter, such that an "antisense" RNA molecule is produced. This "antisense" construct is then transfected into the engineered cell and, upon its expression, produces a RNA molecule that will bind to, and prevent the processing/translation of RNA produced by the targeted gene, in this case the hexokinase gene.

An alternative approach to the reduction of hexokinase action is through a technique known as positive/negative selection. This technique involves selection for homologous recombination of a hexokinase gene segment that renders the endogenous hexokinase gene nonfunctional.

In other embodiments, the present invention is directed to a method of providing a glucose-responsive insulin-secreting capability to a mammal in need of such capability. The method includes generally implanting engineered cells which secrete insulin in response to glucose into such a mammal. It is proposed by the inventor that techniques presently in use for the implantation of islets will be applicable to implantation of cells engineered in accordance with the present invention. One method involves the encapsulation of engineered cells in a biocompatible coating. In this approach, cells are entrapped in a capsular coating that protects the encapsulated cells from immunological responses, and also serves to prevent uncontrolled proliferation of clonal engineered cells. A preferred encapsulation technique involves encapsulation with alginate-polylysine-alginate. Capsules made employing this technique generally contain several hundred cells and have a diameter of approximately 1 mm.

An alternative approach is to seed Amicon fibers with engineered cells. The cells become enmeshed in the fibers, which are semipermeable, and are thus protected in a manner similar to the micro encapsulates (Altman, et al., 1986).

After successful encapsulation or fiber seeding, the cells, generally approximately 1,000–10,000, may be implanted intraperitoneally, usually by injection into the peritoneal cavity through a large gauge needle (23 gauge).

A variety of other encapsulation technologies have been developed that are proposed by the present inventor will be applicable to the practice of the present invention (see, e.g., Lacy et al., 1991; Sullivan et al., 1991; WO 9110470; WO 9110425; WO 9015637; WO 9002580; U.S. Pat. Nos. 5,011, 472; 4,892,538; WO 8901967, each of the foregoing being incorporated by reference). The company Cytotherapeutics has developed encapsulation technologies that are now commercially available that will likely be of use in the application of the present invention. A vascular device has also been developed by Biohybrid, of Shrewsbury, Mass., that may have application to the technology of the present invention.

In regard to implantation methods which may be employed to provide a glucose-responsive insulin-secreting capability to a mammal, it is contemplated that particular advantages may be found in the methods recently described by Lacy et al. (*Science,* 254:1782–1784, 1991) and Sullivan et al. (*Science,* 252:718–721, 1991), each incorporated herein by reference. These concern, firstly, the subcutaneous xenograft of encapsulated islets, and secondly, the long-term implantation of islet.tissue in an "artificial pancreas" which may be connected to the vascular system as an arteriovenous shunt. These implantation methods may be advantageously adapted for use with the present invention by employing engineered cells, as disclosed herein, in the place of the "islet tissue" of the prior art methods.

In still further embodiments, the present invention is directed to methods of detecting the presence of diabetes-associated, or islet-cell directed, antibodies in a sample as a means of assessing the occurrence or risk of diabetes onset. For uses in connection with diagnostic or antibody detection aspects of the present invention, it is contemplated that numerous additional types of engineered cells will prove to be important, particularly those which exhibit an epitope of a selected antigen on their cell surface. Exemplary antigens include particularly GLUT-2, and also glutamic acid decarboxylase (the 64 KD islet antigen and the less antigenic 67 kD form), insulin, proinsulin, islet 38 KD protein, 65 kDa heat shock protein, selected immunoglobulins, insulin receptors or other types of islet cell antigens, whether cytoplasmic or surface. However, it may be desirable to employ cells that do not secrete insulin, in that antibody reactivity with insulin has been associated with false positive reactions.

Generally speaking, the cells are prepared by introducing genes expressing relevant epitopes into cultured cell lines that can be grown in unlimited quantity. However, in the context of immunologically-based detection methods there is no requirement that the cells be glucose-response or have insulin-secreting capability. All that is required is that the these cells express on their surface an epitope associated either with the onset of diabetes or, more generally, an islet cell epitope. Furthermore, there is no requirement that the cell actually express the entire protein, in that all that is ultimately required is that the cell express an epitope that is recognized by the antibody that is sought to be detected. Therefore, the invention contemplates that subfragments which comprise antigenic epitopes may be employed in place of the complete antigenic protein.

The first step of the detection methods of the invention will generally include obtaining a biological sample suspected of containing diabetes-associated or islet cell-directed antibodies. Generally speaking, the biological sample will comprise serum, plasma, blood, or immunoglobulins isolated from such samples. However, the method will be applicable to any sample containing antibodies, regardless of its source or derivation.

Next, the sample is contacted with an engineered cell expressing a diabetes-associated or islet cell-expressed epitope, under conditions effective to allow the formation of an immunocomplex between the expressed epitope and antibodies that may be present in the sample. This aspect is not believed to be particularly critical to the successful practice of the invention in that any incubation technique or conditions that favor immunocomplex formation may be employed. Preferred conditions include incubation of the cells with serum in isotonic media such as phosphate buffered saline or Hanks balanced salt solution.

Lastly, the method is completed by testing for the formation of an immunocomplex between the diabetes-associated or islet cell epitopes expressed by the cell and antibodies present in the sample, wherein a positive immunoreaction indicates the presence of the respective antibody in the sample. The testing method is not believed to be crucial to the overall success of the invention. Many types of testing procedures for detecting immunocomplex formation are known in the art and are applicable, including RIA, EIA, ELISA, indirect immunofluorescence, and the like. In general, all that is required is a testing/detection procedure that allows one to identify an interaction of immunoglobulins present in the sample and epitopes expressed on the surface of the engineered cell.

Certain approaches to the foregoing method will provide particular advantages. One such approach involves contacting the immunocomplexed cell with a molecule having binding affinity for the immunocomplexed antibody. The binding molecule is, generally speaking, any molecule that is capable of binding the immunocomplexed antibody, and that is detectable. Exemplary binding ligands include protein A, anti-immunoglobulin antibodies, protein G, or even complement. Preferably, the binding ligand includes an associated label that allows for the convenient detection of immunocomplexed antibodies. Typical labels include radioactive materials, fluorescent labels, and enzymes. Often, one may achieve advantages through the use of an enzyme such as alkaline phosphatase, peroxidase, urease, β-galactosidase or others that can be detected through use of a calorimetric substrate.

Other specific embodiments may include the use of associating ligands such as biotin, which can complex with avidin or streptavidin and thereby bring the enzyme or other label into association with the antibody or binding ligand.

The detection of immunocomplexed cells through the use of a label may be further improved, and even automated, through the application of cell sorter technology that can identify or quantify cells having associated immunocomplexed antibodies. Particularly preferred is the use of a fluorescent label in conjunction with sorting of cells on a fluorescence-activated cell sorter. The inventors have found that such a system can screen 40–50 sera per hour using a single fluorescence-activated cell sorter.

In other embodiments, one may simply employ a microscope slide test wherein cells are grown on polylysine coated slides, exposed to a test sample and then treated with an appropriate reagent capable of detecting immunocomplex formation. The presence of complexes can then be determined by direct viewing in a microscope, especially when the detecting reagent is an antibody that is labeled with a fluorescent marker.

An extension of such embodiments concerns the delineation of the specific epitope (or epitopes) within an antigenic protein, for example GLUT-2, that is recognized by antibodies in the sera of patients with diabetes. It is proposed that mutant or chimeric protein molecules can be constructed and expressed in recombinant AtT-20 cells, and used to investigate the binding of patients' antibodies, as described above. The failure of antibodies to bind to a mutant molecule after a specific deletion, or likewise, the ability of antibodies to bind to a chimeric molecule after a specific insertion, would allow the identification of the diabetes-specific epitope. Candidate epitopes include multiple extracellular "loop" regions of the GLUT-2 molecule. Once such an epitope is identified, synthetic peptides corresponding to the specific region of the protein sequence can be produced and used to develop simpler diagnostic procedures, for example, utilizing ELISAs or RIAs to detect the formation of an antibody/peptide complex.

It is further believed that the foregoing method may be employed as a technique for selection of engineered clonal cells that express epitopes recognized by autoantibodies. That is, one may prepare a series of clones which comprise, for example, cDNA prepared to islet cell mRNA, express these DNAs in a recombinant cell and screen the resultant recombinant cells with a known antibody composition to identify diabetes associated antigens in addition to those specific antigens discussed above.

In still further embodiments, the invention concerns a method for detecting the presence of diabetes-associated antibodies in a biological sample, such as a sample of serum, plasma, blood, or in immunoglobulins isolated therefrom.

This method comprises contacting the sample suspected of containing diabetes-associated antibodies with intact GLUT-2-expressing cells under conditions effective to allow the interaction of any antibodies which may be present with GLUT-2, and then determining the degree of glucose uptake by the cells. Inhibition of glucose uptake indicates the presence of diabetes-associated antibodies in the sample.

Preferred cells for use in such embodiments are GLUT-2-expressing engineered cells, and particularly, GLUT-2-expressing AtT20$_{ins}$ cells. Suitable conditions for assays of this kind include incubating the cells with an IgG sample and determining the degree of glucose uptake using 3-O-methyl-β-D-glucose.

Further important embodiments concern methods of using the engineered cells of the present invention in the production of insulin, and particularly, in the production of human insulin which can be used in the treatment of IDDM. In certain aspects, the engineered artificial β cells are grown in culture and then contacted with a buffer containing glucose, thus stimulating the cells to produce and secrete insulin which can be collected and purified from the surrounding media. For use in connection with this aspect of the present invention, CTG-6 engineered cells are contemplated to be of parprepared to seut any cell prepared to secrete insulin in response to glucose may be employed.

The inventor has discovered that a particularly useful approach to the production of human insulin in the above manner is the glucose-stimulation of artificial β cells grown in liquid culture. As such, the recombinant cells are contained within a column and subjected to perfusion with a buffer at a physiological pH, such as Krebs Ringer salt (KRS) solution, pH 7.4. To stimulate the production and secretion of insulin, the column of cells is perifused with a glucose-containing buffer, such as KRS, 5 mM glucose. At this stage, the insulin-containing eluent from the column is collected, which provides ideal starting material for the purification of increased amounts of high-quality insulin for human use.

An alternative strategy for the isolation and purification of human insulin for use in IDDM therapy is to purify insulin directly from CGT-6 cells or other GLUT-2 transfected AtT-20 cell lines. This is now a viable possibility as the present inventors have demonstrated that GLUT-2 transfection causes an increase in intracellular insulin of approximately 5-fold in CGT-6 cells. These recombinant cells thus contain sufficient insulin to enable the large scale production of human insulin from CGT-6-like cells possible.

BRIEF DESCRIPTION OF THE DRAWINGS

FIG. 3A: Measurements of 3-O—CH$_3$ glucose uptake as a function of glucose concentration for untransfected AtT-20ins cells (parental) and GLUT-2 transfected lines CGT-5 and CGT-6. The symbol legend is shown in the upper left corner of this panel. FIG. 3B: Reciprocal plot of glucose uptake versus 3-O—CH$_3$ glucose concentration for GLUT-2 transfected lines CGT-5 and CGT-6. The calculated Km and Vmax values for glucose transport and the symbol legends are given in the upper left corner of the panel. FIG. 3C: Reciprocal plot of glucose uptake versus 3-O—CH$_3$-glucose concentration for untransfected AtT-20ins cells (parental cell line). The calculated Km and Vmax values for glucose transport are indicated. Note the difference in the scales between panels B and C.

FIG. 4A: Insulin release was measured from untransfected (AtT-20ins) and GLUT-2 transfected (CGT-6) AtT-20ins lines incubated with varying glucose concentrations over the range of 0–20 mM, or with 0.5 μM forskolin (F) or 0.5 μM forskolin+2.5 mM glucose (F+G) for a period of three hours. Data are normalized to the total cellular protein present in each secretion well and represent the mean±SEM for 3–9 independent secretions per well condition. *, p<0.001 compared to secretion at 0 mM glucose; #, p=0.002 compared to secretion at 0 mM glucose. FIG. 4B: Insulin release was measured from untransfected (AtT-20ins) and GLUT-2 transfected (CGT-6) AtT-20ins lines incubated with 0.5 μM forskolin (Fors) and 2.5 mM glucose (Glc) in combinations indicated by the legend. Data are normalized to total cellular DNA in each secretion well and are expressed as the mean±SEM for 3–9 independent measurements. Statistically significant increases in secretion relative to the -Glc, -Fors control are indicated by the symbol * (p<0.001).

In FIG. 5B, a similar experiment was performed with parental AtT-20ins cells not expressing GLUT-2. In these cells, no difference is seen between the naked antibody and antibody preabsorbed with GLUT-2 expressing cells.

FIG. 6A, FIG. 6B and FIG. 6C. Preliminary data on patient serum. FIG. 6A shows the fluorescence spectrum of GLUT-2 transfected AtT-20ins cells incubated with the second antibody (phycoerythrin labeled anti-human globulin) alone. In FIG. 6B, the GLUT-2 transfected cells have been incubated with serum isolated from a normal patient, resulting in a shift in the fluorescence intensity relative to the control in FIG. 6A. In FIG. 6C, cells are incubated with serum from a patient with new-onset Type I diabetes, resulting in an even greater shift.

FIG. 7A, FIG. 7B and FIG. 7C. Effects of IgG samples on glucose uptake. The effects of purified IgG from nondiabetic subjects (closed circles) and patients with new-onset IDDM (open circles) on the uptake of 3-O-Methyl-β-D-Glucose by dispersed rat islet cells (FIG. 7A), GLUT-2-expressing AtT20$_{ins}$ cells (FIG. 7B), and GLUT-1-expressing AtT20$_{ins}$ cells (FIG. 7C) were determined. Data points for islet cells and GLUT-2-expressing AtT20$_{ins}$ cells are the mean (±SE) uptake of 3-O-methyl-β-D-glucose by each cell type after incubation with purified IgG from 6 nondiabetic human sera and 7 new-onset IDDM patients. Data for GLUT-1-expressing AtT20$_{ins}$ cells were from 5 nondiabetic individuals and 6 new-onset IDDM patients. The rate difference Between curves with IgG from nondiabetic sera and sera from IDDM patients in islet cells and GLUT-2-expressing AtT20$_{ins}$ cells are significant at p<0.05.

DETAILED DESCRIPTION OF THE PREFERRED EMBODIMENTS

ENGINEERING OF "ARTIFICIAL" β CELLS

Figure 1:
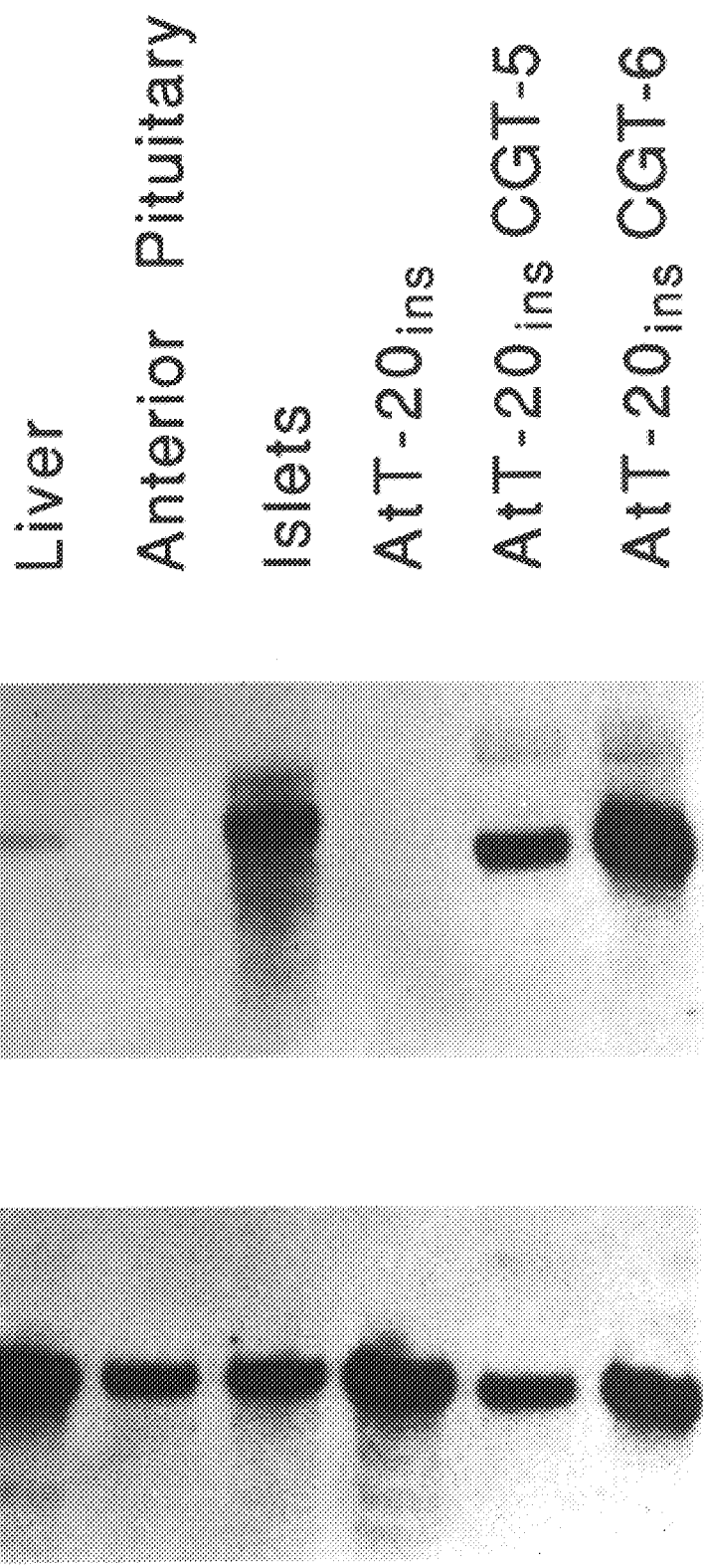
FIG. 1. Northern blot demonstrating the presence of GLUT-2 mRNA in tissues and AtT-20ins cell lines. Each lane contains 6 μg of total RNA. Samples were prepared from liver, anterior pituitary and islet tissue samples, as well as from untransfected (AtT-20ins) and GLUT-2 transfected (AtT-20ins CGT-5 and CGT-6) AtT-20ins cell lines. The blot was probed with radiolabeled antisense GLUT-2 cRNA, and as a control for gel loading, with an antisense oligonucleotide probe for 18S rRNA (Chen, et al., 1990).

Insulin dependent diabetes mellitus (IDDM) is caused by autoimmune destruction of insulin producing β-cells. Islet transplantation has been extensively investigated as a strategy for curing IDDM, but suffers from the difficulties associated with procuring enough tissue. The present invention is based in part on the inventor's recognition that the problem of islet supply could potentially be circumvented if a non-islet cell type could be engineered to secrete insulin in response to metabolic signals, since such cells could be grown in unlimited quantity in vitro. Such cells could ultimately replace daily insulin injections as therapy for Type I diabetes.

The participation of the pancreatic islets of Langerhans in fuel homeostasis is mediated in large part by their ability to respond to changes in circulating levels of key metabolic fuels by secreting peptide hormones. Accordingly, insulin secretion from islet β-cells is stimulated by amino acids, three-carbon sugars such as glyceraldehyde, and most prominently, by glucose. While these diverse secretagogues may ultimately work through a final common pathway involving alterations in K+ and Ca++ channel activity and increases in intracellular Ca++ (Prentki, et al., 1987; Turk, et al., 1987), the biochemical events leading from changes in the levels of a particular fuel to insulin secretion are initially diverse. In the case of glucose, transport in the β-cell and metabolism of this sugar are absolute requirements for secretion, leading to the hypothesis that its specific stimulatory effect is mediated by and proportional to its flux rate through glycolysis and related pathways (Ashcroft, 1980; Hedeskov, 1980; Meglasson, et al., 1986; Prentki, et al., 1987; Turk, et al., 1987; Malaisse, et al., 1990). Strong support for this view comes form the finding that non-metabolizable analogues of glucose such as 3-O-methyl or 2-deoxy glucose fail to stimulate insulin release (Ashcroft, 1980; Meglasson, et al., 1986).

A substantial body of evidence has accumulated implicating a specific facilitated-diffusion type glucose transporter known as GLUT-2, and the glucose phosphorylating enzyme, glucokinase, in the control of glucose metabolism in islet β-cells. Both proteins are members of gene families; GLUT-2 is unique among the five-member family of glucose transporter proteins (GLUTs 1–5; Bell, et al., 1990; Thorens, et al., 1990a) in that is has a distinctly higher Km and Vmax for glucose transport. Glucokinase (also known as Hexokinase IV) is the high Km, high Vmax counterpart of GLUT-2 among the family of hexokinases (Weinhouse, 1976). Importantly, both proteins have affinities for glucose that allow dramatic changes in their activities over the physiological range of glucose. This has led to the hypothesis that these proteins work in concert as the "glucose-sensing apparatus" that modulates insulin secretion in response to changes in circulating glucose concentrations by regulating glycolytic flux (Newgard, et al., 1990; Johnson, et al., 1990a).

In normal β-cells, glucose transport capacity is in excess relative to glycolytic flux. Thus, the GLUT-2 transporter likely plays a largely permissive role in the control of glucose metabolism, while glucokinase represents the true rate-limiting step (Meglasson and Matchinsky, 1986; Newgard, et al., 1990). Implicit in this formulation, however, is the prediction that severe underexpression of GLUT-2 will result in loss of glucose-stimulated insulin secretion in islets, an idea that has recently received strong experimental support from studies with spontaneous (Johnson, et al., 1990b; Orci, et al., 1990) as well as experimentally induced (Chen, et al., 1990; Thorens, et al., 1990b) animal models of β-cell dysfunction.

IDDM has traditionally been treated by insulin replacement, either classically, by external administration, or experimentally, by transplantation of islets or pancreas fragments. The latter strategy is not likely to be broadly applicable because of the difficulty and expense associated with the isolation of large numbers of islets. The present invention is directed to an alternative approach, that of using molecular techniques to engineer an "artificial β-cell", i.e., a non-islet cell capable of performing glucose-stimulated insulin secretion, which can be grown in unlimited quantity in vitro.

The anterior pituitary cell line AtT-20ins is preferred because of important similarities to β-cells. First, these cells have been modified for insulin gene expression by stable transfection with a viral promoter/proinsulin cDNA construct (Moore, et al., 1983). Second, AtT-20ins cells are able to process the proinsulin MRNA and preprotein to yield the correctly processed insulin polypeptide. Third, their secretory response to analogues of cAMP compares favorably with the well differentiated hamster insulinoma (HIT) cell line (Moore, et al., 1983). Finally, AtT-20ins cells contain significant amounts of the islet isoform of glucokinase (Hughes, et al., 1991), making this the only tissue other than liver or islets in which glucokinase gene expression has been reported.

On the other hand, AtT-20ins cells differ from islets in two important ways. First, they do not secrete insulin in response to glucose, and second, they express the low Km GLUT-1 glucose transporter MRNA and not GLUT-2 (Hughes, et al., 1991). The inventor hypothesized that the lack of glucose responsiveness in AtT-20ins cells could be explained either by deficient capacity or altered affinity of glucose uptake relative to normal islets. To test this hypothesis, AtT-20ins cells were stably transfected with GLUT-2 cDNA. Surprisingly, the inventor found that cells engineered in this way gained glucose-stimulated insulin secretion and glucose potentiation of non-glucose secretagogue stimulation, albeit with a dose-response curve that is different from normal islets.

Engineering of the AtT-20ins cells generally involved construction of a suitable GLUT-2 expression vector, transfection of AtT-20ins cells with the vector, and selection of stable transfectants. To accomplish this, rat islet GLUT-2 cDNA (Johnson et al., 1990a) was cloned into the vector pCB-7, a derivative of vector pCMV4 (Anderson, et al., 1989), immediately downstream of its cytomegalovirus (CMV) promoter. pCB-7 was constructed by Drs. Michael Roth and Colleen Brewer of the Biochemistry Department, University of Texas Southwestern Medical Center at Dallas and provided as a gift to the inventors. It differs from pCMV-4 in that it contains a hygromycin resistance gene; thus, cells transfected with the pCB7/GLUT-2 construct can be selected for stable integration of the vector DNA into the cell's genome by treatment with hygromycin. AtT-20ins cells were transfected with this construct using electroporation, and stable transfectants were selected with hygromycin.

Expression of GLUT-2 mRNA was evaluated by blot hybridization analysis of AtT-20ins cells, either transfected or untransfected with a cytomegalovirus (CMV) promoter/GLUT-2 hybrid gene, and in extracts of rat liver, islets of Langerhans, and anterior pituitary tissues. A radiolabeled GLUT-2 antisense RNA probe (Johnson, et al., 1990a; Chen, et al., 1990) was hybridized to a blot containing equal amounts of RNA from four GLUT-2 transfected AtT-20ins cell lines (CGT-1, CGT-2, CGT-5, CGT-6), untransfected AtT-20ins cells, and the three primary tissues (FIG. 1). Steady state levels of GLUT-2 mRNA were highest in CGT-5 and CGT-6; the former contained approximately half as much and the latter an equal amount of GLUT-2 mRNA as rat islets, and they contained 10 and 16 times as much, respectively, as rat liver, measured by densitometric scanning and normalization to the signal obtained with an 18S mRNA probe. The transfected lines contained a smaller GLUT-2 transcript than liver or islets (2.2 versus 2.8 kb) because 635 base paris of the 3' untranslated region were removed in the course of cloning the GLUT-2 cDNA into the pCB-7 vector. Lines CGT-1 and CGT-2 exhibited less active expression of GLUT-2. Untransfected AtT-20ins cells and primary anterior pituitary cells did not contain detectable amounts of GLUT-2 mRNA, consistent with the inventor's previous work (Hughes, et al., 1991).

Figure 2:
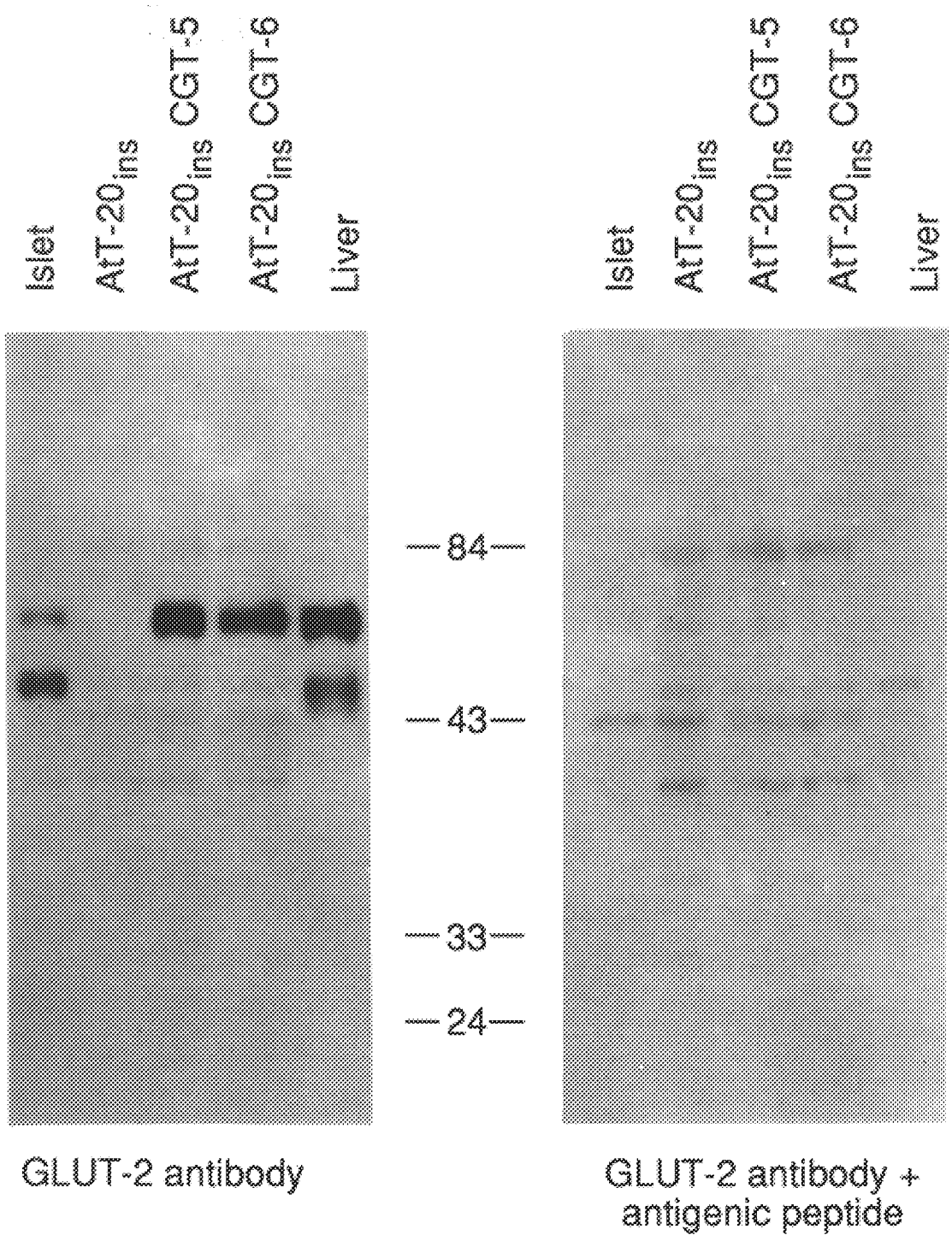
FIG. 2. Immunoblot of GLUT-2 in tissues, untransfected cells (AtT-20ins) and cells transfected with the CMV/GLUT-2 construct (AtT-20ins CGT-5, -6).

In order to evaluate the levels and molecular status of the expressed GLUT-2 protein in transfected AtT-20ins cells, crude membrane fractions were resolved by SDS/PAGE, the separated proteins transferred to nitrocellulose, and GLUT-2 protein detected with an antibody raised against its C-terminal hexadecapeptide sequence (Johnson, et al., 1990b). The antibody recognized two distinct bands in liver and islets, with apparent molecular weights of 70 and 52 kd in liver and slightly different sizes of 72 and 56 kd in islets (FIG. 2, left). Consistent with the RNA blot hybridization data, untransfected AtT-20ins cells were found to lack GLUT-2 protein, while a single intense band of approximately 70 kd was observed in extracts from either of the transfected lines. The specificity of the antibody was demonstrated by the fact that all bands were blocked by preincubation of the antibody with the antigenic peptide (FIG. 2, right).

In light of the observed differences in molecular species of GLUT-2 observed in the cell types studied, the distribution and sorting of the expressed GLUT-2 proteins was evaluated in transfected AtT-20ins cells by immunocytochemical analysis and light microscopy, using the same antibody employed for blot hybridization analysis. In the lines with highest GLUT-2 expression, abundant GLUT-2 expression was detected at the cell membrane. The signal was entirely blocked by preincubation of the antibody with the antigenic peptide and was not seen in untransfected cells or in cells transfected with the vector lacking the GLUT-2 insert. Thus, the transfected AtT-20ins cells not only had the capacity to produce GLUT-2 mRNA and protein but also sort the protein to the cell membrane, as occurs in both islets and liver (Thorens, et al., 1988; Tal, et al., 1990; Orci, et al., 1989, Orci, et al., 1990).

It was further found that the engineered lines with high levels of GLUT-2 expression (CGT-5, CGT-6) transported glucose very rapidly, with an estimated Km for glucose of 18 mM and a Vmax of 19 mmoles/min/liter cell space. In contrast, the untransfected parental AtT-20ins line transported glucose much less efficiently, with an apparent Km for glucose of 2 mM and a Vmax of 0.5, consistent with its expression of the GLUT-1 mRNA (Hughes, et al., 1991), which encodes the low Km glucose transporter found in most clonal cell lines (Flier, et al., 1987; Birnbaum, et al., 1987). The transfected AtT-20ins cells have glucose transport kinetics that are remarkably similar to isolated, dispersed islets of Langerhans, which have a Km of 18 mM for glucose and a Vmax of 24 mmoles/min/liter cell space (Johnson, et al., 1990a). Thus, the GLUT-2 cDNA clearly encodes the protein responsible for the high Km glucose transport activity in islets and liver, and is capable of transferring this activity in to the AtT-20ins cell line. The fact that only the larger protein species of GLUT-2 is detected in transfected AtT-20ins cells indicates that it is an active glucose transporter.

Insulin secretion from GLUT-2 transfected and untransfected cells was measured over a range of glucose concentrations from 0–20 mM. In measuring glucose-stimulated insulin release from AtT-20ins cells and CGT-6 cells, glucose was found to have no significant effect on insulin release from parental AtT-20ins cells, consistent with previous results (Hughes, et al., 1991). AtT-20ins cells transfected with the pCB7 vector lacking a GLUT-2 insert were also found to be unresponsive to glucose. GLUT-2 transfected cells, in contrast, were found to be clearly glucose responsive. A submaximal but statistically significant (p=0.002) increase in insulin release relative to insulin release at 0 mM glucose was observed at the lowest concentration of glucose studied (5 $\mu$M); maximal stimulation of approximately 2.5-fold was observed at all higher concentrations over the range 10 $\mu$M–20 mM (p$\leq$0.001). It is highly unlikely that these results can be attributed to clonal selection of glucose responsive subpopulations of the parental AtT-20ins cells, since cells transfected with vector lacking GLUT-2 failed to respond, while two independent GLUT-2 expressing lines (CGT-5 and CGT-6) gained glucose sensing.

In normal islets, glucose potentiates the insulin secretory response to various $\beta$-cell secretagogues, including agents that increase intracellular cAMP levels (Ullrich and Wollheim, 1984; Malaisse, et al., 1984). The inventor therefore studied the potentiating effect of glucose on insulin secretion in the presence of forskolin, dibutyryl cAMP, and IBMX. Glucose has a modest stimulatory effect on forskolin stimulated insulin release from parental AtT-20ins cells, when the data were expressed either as insulin release/mg cellular protein, or as insulin release/mg cellular DNA. In contrast, glucose had a powerful potentiating effect on forskolin stimulated insulin release from transfected CGT-6 cells. The response was unchanged by glucose concentration over the range of 1–5 mM, and similar potentiating effects of glucose on dibutryl cAMP and IBMX induced secretion were also observed.

Insulin secretion experiments involved static incubation of cells with the secretagogue of interest for three hours, and thus provide little information about the dynamics of insulin release. The inventor thus grew the parental and transfected AtT-20ins cell lines on gelatin beads in liquid culture, allowing their secretory properties to be studies by perfusion with glucose containing media. In this configuration, insulin was released within minutes of the start of glucose perfusion, and the secretion response exhibited a first and second phase as is characteristic of normal β-cells. Maximal stimulation of insulin release occurred during the first 10 minutes of perfusion with glucose (first phase) and was 10-fold greater than baseline (in the absence of glucose).

A remarkable finding of this work is that transfection of AtT-20ins cells with the GLUT-2 cDNA results in a substantial increase in intracellular insulin content, despite the fact that insulin gene expression is driven by the glucose insensitive Rous sarcoma virus long-terminal repeat enhancer/promoter in these cells. Native AtT-20ins cells and the GLUT-2 transfected CGT-6 cells were grown for 3 days in media supplemented with low (1 mM) or high (25 mM) glucose. The CGT-6 cells were found to contain 3.6-fold and 5.4-fold more insulin than the AtT-20ins cells when studied at low and high glucose, respectively ($p<0.001$ for both comparisons). Furthermore, insulin content was approximately double in the CGT-6 cells grown at high glucose compared with the same cells grown at low glucose ($p<0.001$). In contrast, in the untransfected AtT-20ins cells, high glucose caused only a 20% increase in insulin content.

Although the inventor has succeeded in engineering an AtT-20ins cell line with glucose-stimulated insulin secretion, maximal insulin secretion from these cells occurs at a much lower glucose concentration than observed for normal islets, which do not respond at levels less than the fasting glucose concentration of approximately 4–5 mM, and which have not reached maximum secretion at the upper range of physiological glucose (10 mM). The potentiating effect of glucose on forskolin, dibutryl cAMP, or IBMX induced insulin secretion from AtT-20ins cells is also maximal at low glucose. The heightened sensitivity of GLUT-2 transfected AtT-20ins cells to both the direct and potentiating effects of glucose is reminiscent of a number of cell lines derived from insulinoma (β-cell) tumors (Praz, et al., 1983; Halban, et al., 1983; Giroix, et al., 1985; Meglasson, et al., 1987; Clark, et al., 1990). For example, the rat insulinoma cell line RIN 1046-38 is responsive to glucose when studied after short periods of time in cell culture (between passages 6–17), albeit with a maximal response at sub-physiological glucose levels, as in transfected AtT-20ins cells. With longer time in culture (passage number greater than 50), all glucose-stimulated insulin secretion is lost (Clark, et al., 1990). Low passage RIN 1046-38 cells contain both glucokinase and GLUT-2, but lose expression of these genes when studied at higher passages.

The fact that both transfected AtT-20ins cells and RIN1046-38 cells of low passage number respond to subphysiological levels of glucose, despite expression of glucokinase and GLUT-2, suggests that these cells share metabolic determinants that can override the regulatory function of the high Km components. Given that the glucose transport kinetics of normal islets are recapitulated in GLUT-2 transfected AtT-20ins cells, the increased sensitivity of the clonal cells to glucose might alternatively be explained by alteration in regulation of glucose phosphorylation. While hexokinase activity is readily measured in islet cell extracts, this enzyme is thought to be potently inhibited (by as much as 95%) inside the intact islet cell (Trus, et al., 1981; Giroix, et al., 1984). Thus, in the presence of stimulatory concentration of glucose, normal islets have both sufficient glucokinase activity and inhibited hexokinase (the levels of glucose-6-phosphate, an inhibitor of hexokinase, increase during glucose stimulation) to allow the control of glucose metabolism to be tied directly to glucokinase activity (Km of ~10 mM in islets) (Meglasson, et al., 1986).

AtT-20ins cells have glucokinase activity, but it represents only 9% of total glucose phosphorylation in these cells, and only 32% of the activity measured in normal islets (Table 1 in Example I below); the proportions of glucose phosphorylating enzymes in RIN1046-38 cells are similar to those found in AtT-20ins cells (Newgard, C. B., unpublished observations). Hexokinase I, the isoform that is expressed in most clonal cell lines (Arora, et al., 1990) is found bound to mitochondria and in a free cytosolic form (Lynch, et al., 1991); in the former state, the enzyme is less sensitive to glucose-6-phosphate inhibition (Wilson, 1984). Thus, in addition to the fact that AtT-20ins cells have reduced glucokinase activity, they may also have altered regulation of hexokinase such that it becomes the predominant glucose phosphorylating enzyme at any concentration of glucose studied.

The increased sensitivity of GLUT-2 expressing AtT-20ins or RIN cells can be explained as follows. Expression of the GLUT-2 transporter not only increases the Km for transport, but also the transport capacity at all glucose concentrations studied. Our data show that at 2.5 mM glucose, for example, there is an approximately 10-fold increase in glucose uptake in the GLUT-2 transfected cells compared to the parental line (see FIG. 3A). This means that even at glucose concentrations that would be sub-stimulatory for islets, transport into GLUT-2 transfected AtT-20ins cells will be rapid and hexokinase activity (Km for glucose of ~0.01 mM) will be maximal, and the generation of glucose-related secretory signals will be maximized at low glucose as a consequence. The inventor is currently investigating whether the hexokinase:glucokinase ratio can be altered by molecular techniques in GLUT-2 transfected AtT-20ins cells, and if so, whether a glucose dose-response curve resembling that of islets will be gained.

As discussed above, an imbalance in the hexokinase/glucokinase ratio may at times result in maximal insulin secretory response at subphysiological glucose concentrations. The inventor proposes that a more physiologic glucose response may be achieved by "knocking out" hexokinase activity in engineered cells of the present invention. One approach is to co-transfect these cells with antisense hexokinase constructs. This can be achieved, for example, using the CMV vector system described for GLUT-2 transfection, with the exception that the plasmid will contain an alternate resistance gene, such as puromycin or histidinol, since the AtT-20ins cell line is resistant to both neomycin (due to stable integration of the SV40-insulin-neo chimeric construct) and hygromycin (due to stable integration of the CMV-GLUT-2-hygromycin chimeric construct). Recently, the hexokinase isozyme expressed in mouse hepatoma cells has been cloned and characterized (Arora, et al., 1990) and shown to be approximately 92% identical to the hexokinase I sequences derived from rat brain (Schwab, et al., 1989) and human kidney (Nishi, et al., 1988).

In order to generate antisense probes with exact sequence identity to the homologue of hexokinase I being expressed to the engineered cell, the hexokinase variant present in the cell was converted to cDNA by reverse transcribing the MRNA and amplification of the DNA product, a procedure recently employed in the inventor's laboratory for amplification of glucokinase mRNA from islets, RIN cells, AtT-20ins cells, and primary anterior pituitary cells (Hughes, et al., 1991). The oligonucleotides used for amplification were based on the published sequence of the mouse hepatoma hexokinase I (Arora, et al., 1990). The oligonucleotides included restriction enzyme recognition sequences at their 5' ends to facilitate directional cloning of the amplified cDNA into the selected vector in an antisense orientation.

Because the vector contains both the transcription termination and polyadenylation signal sequences downstream of the cloning cassette, processing of the antisense transcripts should proceed normally. Proof of this comes from the data derived with the GLUT-2/CMV construct, which was prepared using a restriction site in the 3' untranslated region of the GLUT-2 cDNA that removed some 600 bases of the 3' tail, a maneuver that had no effect on transcription or translation of the GLUT-2 mRNA. One may desire to select various, different portions of the hexokinase sequence, since various investigators have reported success with antisense technology with full length antisense messages, or partial transcripts that either target the ATG initiator codon and surrounding sequence or the 3' untranslated region and poly A tail (Walder, 1988).

It is proposed that engineered lines may be transfected with antisense constructs by electroporation. After appropriate selection to obtain colonies that have stably integrated the antisense hexokinase construct into their genome, expression of the antisense mRNA can be evaluated by hybridization to labeled sense RNA, e.g., prepared with the pGEM vector system (Promega). Blot hybridization analysis may be carried out not only with the probe corresponding to the antisense construct, but to regions outside as well, since cellular factors known to unwind RNA: RNA duplexes results in modification of that RNA, thus interfering with its detection on Northern blots (Walder, 1988). One may assess whether the presence of antisense mRNA is capable of affecting the level of hexokinase protein(s) through the use of antibodies against relevant hexokinase sequence(s).

Should the foregoing general antisense approach fail to provide adequate hexokinase suppression in the particular system selected, modified antisense oligonucleotides may be employed. For example, an antisense oligonucleotide may be prepared to sequences surrounding and/or containing the ATG initiation codon, for example, and introduced into cells by simply incubating the cells in media containing the oligonucleotide at high concentration. This approach bypasses uncertainties about the stability of longer antisense hexokinase transcripts synthesized from the construct and should provide suppression of hexokinase activity for a period of time sufficient to assess the functional consequences. On the negative side, the oligonucleotide antisense procedure can only cause a transient reduction in endogenous expression, and is thus not applicable to the engineering of a stable "artificial" β-cell.

A second alternative that bypasses the issue of effectiveness of antisense strategies altogether would be to knock out the endogenous hexokinase gene of interest cells using a positive/negative selection protocol (Mansourt, et al., 1988; Capecchi, 1989; Zheng, et al., 1990) to select for homologous recombination of a hexokinase gene segment that renders the endogenous hexokinase gene nonfunctional. This approach involves cloning of at least a segment of the hexokinase gene(s) expressed in the engineered cells either by library screening or PCR™ amplification, and construction of a vector that contains a genomic fragment, preferably containing exons that encode the putative ATP or glucose binding sites (Arora, et al., 1990; Schwab, et al., 1989; Nishi, et al., 1988; Andreone, et al. 1989). These also are then interrupted by insertion of an antibiotic resistance gene (e.g., puromycin) and cloned into a targeting vector adjacent to a copy of, e.g., the herpes simplex virus (HSV) thymidine kinase gene.

The plasmid is then introduced into cells by electroporation and homologous recombination events are selected for by incubation of the cells in puromycin and FIAU, a recently described thymidine kinase substrate (Capecchi, 1989; available from Dr. Richard White, Bristol Myers/Squibb, Walingford, Conn.). The action of FIAU is exerted as follows. If recombination occurs at a nonhomologdus site, the viral thymidine kinase gene is retained in the genome and expressed, rendering cells extremely sensitive to FIAU. If the disrupted gene is inserted at its homologous site (the endogenous hexokinase gene), in contrast, the viral thymidine kinase gene is lost, and the cells are tolerant of the drug. While homologous recombination in mammalian cells is a relatively rare event, the selection of strategy is sound, and has recently been applied to mammalian tissue culture cells (Zheng, et al., 1990).

Although glucokinase activity is present in AtT-20ins cells, the activity of 0.7 U/g protein is only about 25% of the activity in normal islet cells, which contain approximately 3.1 U/g protein. One may therefore desire to increase the glucokinase activity of engineered cells, using a cDNA clone for the islet isoform of glucokinase (Newgard, 1990; Hughes et al., 1991) and the strategies and vector systems described above. If the assumption about hexokinase overexpression is correct, it may be necessary to increase glucokinase expression in engineered cells having a reduced hexokinase activity in order to observe any effects on glucose responsiveness. Note that creation of a GLUT-2$^+$, insulin$^+$, glucokinase-overexpressing, hexokinase cell line will require cotransfection of some of the relevant constructs, since limited numbers of resistance-gene containing plasmids are available. Efficient cotransfection can be expected when using either electroporation or CaPO$_4$ precipitation transfection strategies (Sambrook, et al., 1989).

It is proposed that engineered cells that respond to glucose by secreting insulin may be introduced into animals with insulin dependent diabetes. Although ideally cells are engineered to achieve glucose dose responsiveness more closely resembling that of islets, it is believed that implantation of the CGT-5 or CGT-6 GLUT-2 expressing cells will also achieve advantages in accordance with the invention. It should be pointed out that the experiments of Madsen and coworkers have shown that implantation of poorly differentiated rat insulinoma cells into animals results in a return to a more differentiated state, marked by enhanced insulin secretion in response to metabolic fuels (Madsen, et al., 1988). These studies suggest that exposure of engineered cell lines to the in vivo milieu may have some effects on their response(s) to secretagogues.

Engineered cells may be implanted using the alginate-polylysine encapsulation technique of O'Shea and Sun (1986), with modifications as recently described by Fritschy, et al. (1991). The engineered cells are suspended in 1.3% sodium alginate and encapsulated by extrusion of drops of the cell/alginate suspension through a syringe into CaCl$_2$. After several washing steps, the droplets are suspended in polylysine and rewashed. The alginate within the capsules is then reliquified by suspension in 1 mM EGTA and then rewashed with Krebs balanced salt buffer. Each capsule should contain several hundred cells and have a diameter of approximately 1 mm.

Implantation of encapsulated islets into animal models of diabetes by the above method has been shown to significantly increase the period of normal glycemic control, by prolonging xenograft survival compared to unencapsulated islets (O'Shea, et al., 1986; Fritschy, et al., 1991). Also, encapsulation will prevent uncontrolled proliferation of clonal cells. Capsules containing cells are implanted (approximately 1,000–10,000/animal) intraperitoneally and blood samples taken daily for monitoring of blood glucose and insulin.

Recently, further methods for implanting islet tissue into mammals have been described (Lacy et al., 1991; Sullivan et al., 1991; each incorporated herein by reference). Firstly, Lacy and colleagues encapsulated rat islets in hollow acrylic fibers and immobilized these in alginate hydrogel. Following intraperitoneal transplantation of the encapsulated islets into diabetic mice, normoglycemia was reportedly restored. Similar results were also obtained using subcutaneous implants that had an appropriately constructed outer surface on the fibers. It is therefore contemplated that engineered cells of the present invention may also be straightforwardly "transplanted" into a mammal by similar subcutaneous injection.

The development of a biohybrid perfused "artifical pancreas", which encapsulates islet tissue in a selectively permeable membrane, has also been reported (Sullivan et al., 1991). In these studies, a tubular semi-permeable membrane was coiled inside a protective housing to provide a compartment for the islet cells. Each end of the membrane was then connected to an arterial polytetrafluoroethylene (PTFE) graft that extended beyond the housing and joined the device to the vascular system as an arteriovenous shunt. The implantation of such a device containing islet allografts into pancreatectomized dogs was reported to result in the control of fasting glucose levels in 6/10 animals. Grafts of this type encapsulating engineered cells could also be used in accordance with the present invention.

An alternate approach to encapsulation is to simply inject glucose sensing cells into the scapular region or peritoneal cavity of diabetic mice or rats, where these cells are reported to form tumors (Sato, et al., 1962). Implantation by this approach may circumvent problems with viability or function, at least for the short term, that may be encountered with the encapsulation strategy. This approach will allow testing of the function of the cells in experimental animals but obviously is not applicable as a strategy for treating human diabetes.

With what is learned from engineering of clonal cell lines, it may ultimately be possible to engineer primary cells isolated from patients. Dr. Richard Mulligan and his colleagues at the Massachusetts Institute of Technology have pioneered the use of retrovirus vectors for the purposes of introducing foreign genes into bone marrow cells (see, e.g, Cone, et al., 1984; Danos, et al., 1988). The cells of the bone marrow are derived from a common progenitor, known as pluripotent stem cells, which give rise to a variety of blood borne cells including erythrocytes, platelets, lymphocytes, macrophages, and granulocytes. Interestingly, some of these cells, particularly the macrophages, are capable of secreting peptides such as tumor necrosis factor and interleukin 1 in response to specific stimuli. There is also evidence that these cells contain granules similar in structure to the secretory granules of β-cells, although there is no clear evidence that such granules are collected and stored inside macrophages as they are in β-cells (Stossel, 1987).

Nevertheless, it may ultimately be possible to use the recombinant DNA for glucose transporters and glucose phosphorylating enzymes in combination with the. recombinant insulin gene in a manner described for clonal cells to engineer primary cells that perform glucose-stimulated insulin secretion. This approach would completely circumvent the need for encapsulation of cells, since the patient's own bone marrow cells would be used for the engineering and then re-implanted. These cells would then develop into their differentiated form (i.e., the macrophage) and circulate in the blood where they would be able to sense changes in circulating glucose by secreting insulin.

USE OF ENGINEERED CELLS FOR DIAGNOSIS OF IDDM PRIOR TO ONSET

As discussed above, antibodies against islet proteins have been identified in individuals with new-onset IDDM. The appearance of these antibodies likely precedes the period of islet β-cell destruction and consequent loss of insulin production. In recent years, significant progress has been made in the identification of the specific proteins that are recognized by the immune system. Expression of one such potential antigen, the GLUT-2 islet β-cell glucose transporter, in non-islet cell lines, as described herein now allows us to test the immune response of patient sera wit a specific islet antigen. Other particular epitopes contemplated by the inventor as being preferred include epitopes of cytoplasmic and surface islet cell antigens (Lernmark, 1982), insulin (Srikanta et al., 1986), proinsulin (Kuglin et al, 1988), islet 64 Kd and 38 Kd protein (Baekkeskov et al., 1982), immunoglobulins (DiMario et al., 1988), mammalian 65 Kd heat shock protein (Elias et al., 1991), and even insulin receptors (Ludwig et al., 1987).

The inventors propose that cells engineered for specific expression of one of the foregoing epitopes, or for any epitope that may subsequently be identified in autoimmune diabetes, may be employed in diagnostic tests for diabetes. The principle of such a test involves reaction of the antibodies in a patients' serum with cells expressing the antigen (s) of choice, or epitope(s) of such an antigen, and subsequent detection of the antigen/antibody complex by reaction with a second antibody that recognizes human immunoglobulins (antibodies). A test would be scored as positive if the serum being tested reacts with the cells engineered for expression of the antigen of interest, but not with the parental (non-engineered) cell line. The reaction of the patient's serum with the expressed antigen is measured indirectly by virtue of the fact that the anti-immunoglobulin antibody used is "labeled" or "tagged" with a molecule that allows its detection by direct inspection or mechanical measurement. The most common "tags" that are linked to commercially available preparations of anti-human immunoglobulin are fluorescent molecules such as fluorescein or tetramethyl rhodamine.

As disclosed hereinbelow, the use of engineered cells expressing the GLUT-2 antigen in diagnostic assays is greatly advantageous in that it allows rapid, efficient and reproducible analyses of patients' sera. Engineered GLUT-2-expressing cells, such as GLUT-2-expressing AtT20$_{ins}$ cells may be used in diagnostic assays based either on immunocomplex formation, or on the inhibition of glucose uptake, for example, using 3-O-methyl-β-D-glucose. However, it will be understood that engineered cells expressing the GLUT-1 antigen will also have utility. In particular, they may be used as 'control' cells in diagnostic tests since no reaction of IDDM sera is detected with GLUT-1-expressing cells in these assays.

Regarding immunocomplex formation, two methodologies are available for measuring the fluorescent signal resulting from formation of an antigen-antibody-anti-antibody complex. The first is simple direct inspection of cells by fluorescence microscopy. In this procedure, cells are adhered to poly-L-lysine coated microscope slides or cover slips. The cells are then fixed lightly by treatment with 0.5% paraformaldehyde or left untreated. Treatment of the cells with paraformaldehyde will cause changes in membrane structure of cells, resulting in changes in the conformation of antigen molecules. For some, but not all antibodies, alteration of antigen conformation in this way will allow a tighter association of the antibody and antigen. Engineered and control cells are then exposed to either crude serum or purified immunoglobulins (IgGs) from patients to be tested for antibodies against the expressed antigen. After washing, the cells are exposed to an antibody recognizing human IgGs and the antigen/antibody/anti-antibody complexes are visualized in a microscope by excitation of the fluorescent tag by exposure to light of an appropriate wavelength.

An alternative and more quantitative approach is to use a fluorescence activated cell sorter (FACS) to score immune complex formation. In this procedure, cells are treated with patient serum and labeled second antibody much as described for the microscope slide approach except that the incubations are done with the cells in suspension rather than attached to a slide. After treatment with the anti-human IgG antibody, cells are loaded into the FACS, which passes the cells one-by-one past a light source set at a wavelength that will excite the fluorescent marker of the second antibody. The cells then pass a detector which measures the fluorescence emission from the cells. Data are plotted as a histogram of fluorescence intensity. A positive antibody/antigen/anti-antibody reaction will result in an increase in fluorescence in most of the cells in a test. In contrast, exposure of cells to sera that lack antibodies against the specific antigen being presented will result in little fluorescence. The utility of the FACS is that it provides a display of the fluorescence intensity of all of the cells in a sample and plots the data as the distribution of fluorescence intensities. Thus a positive sample will have a peak in cell distribution at a position on the graph that is shifted to the right (corresponding to a greater fluorescence intensity) relatively to a sample that is not reactive.

To date the inventors have observed a noticeable increase in the fluorescent signal in GLUT-2 transfected AtT-20ins cells treated with sera from patients with IDDM compared with normal sera with both the microscopic and FACS techniques. Importantly, an antibody raised against an exposed (extracellular) region of the GLUT-2 molecule has been found by the inventors to cause a shift (increase) in fluorescence that is similar to the shift caused by the diabetic sera. Thus, GLUT-2 appeared to be a particularly useful epitope for the identification of new-onset IDDM patients and even prediction of diabetes onset.

In copending application Ser. No. 483,224, filed Feb. 20, 1990, it is demonstrated that the sera of IDDM patients includes autoantibodies that are capable of inhibiting the uptake of glucose by β-cells. This observation led to the development of a bioassay for identifying individuals at risk for the development of IDDM. Unfortunately, this method is somewhat cumbersome. Accordingly various approaches were taken to simplify and improve this diagnostic assay, centering on the development of an immunological-based assay.

Among the approaches studied included ELISA- and Western blot-based assays, as opposed to measurement of glucose transport rates. Attempts at using these techniques were successful, but the problem at this level was the numbers of false positive normal individuals that were identified. Since there was a much better separation of the normal and diabetic populations observed using the glucose transport assay, it was hypothesized that the use of intact cellular protein in the transport assay, as opposed to the use of denatured protein in the Western blot and ELISA techniques, might account for the difference.

To test this hypothesis, artificial β-cells of the present invention were tested in the glucose transport assay. In these studies, it was shown that IgG from IDDM patients effectively inhibited glucose transport in the artificial β-cells, while no effect was seen with IgGs from normal individuals. Moreover, no effect of IgGs from new-onset Type 1 individuals on glucose uptake was observed against cells that did not contain the GLUT-2 protein.

These data led to the development of a flow cytometry-based immunofluorescence assay for antigen-antibody interaction between the patient's autoantibodies and the glucose transporter mechanism. Initial attempts to develop such a system met with variable success. It was suspected that this variability might be due to the day-to-day handling of samples. Accordingly, a protocol was developed to ensure uniform growth of the cells, harvesting of the cells and treatment of the cells under conditions as close as possible to the transport assay. These conditions were as follows:

1. AtT 20 GT6 cells were grown for 72 hours following a 1:10 split at confluence of the seed culture.
2. Cells were harvested from plates by scraping with a rubber policeman into Dulbecco's phosphate-buffered saline at pH 7.6.
3. The cells were resuspended to a density of approximately $10^6$ cells/ml, washed by centrifugation at 500×g in Dulbecco's phosphate-buffered saline, and incubated with shaking for 15 minutes at 37° C. followed by 1 hour at 4° C. in 150 μl of patient serum.
4. Following two washes by centrifugation at 500×g in Dulbecco's phosphate-buffered saline, the cells were resuspended in 200 μl of R-phycoerythrin-labeled goat antihuman IgG (heavy chain specific), vortexed lightly, and incubated for 1 hour at 4° C. on a dual action shaker.
5. Following two washes by centrifugation at 500×g in Dulbecco's phosphate-buffered saline, the cells were resuspended in 500 μl of Dulbecco's phosphate-buffered saline and analyzed for antigen-antibody interaction using a flow cytometer.

Figure 8:
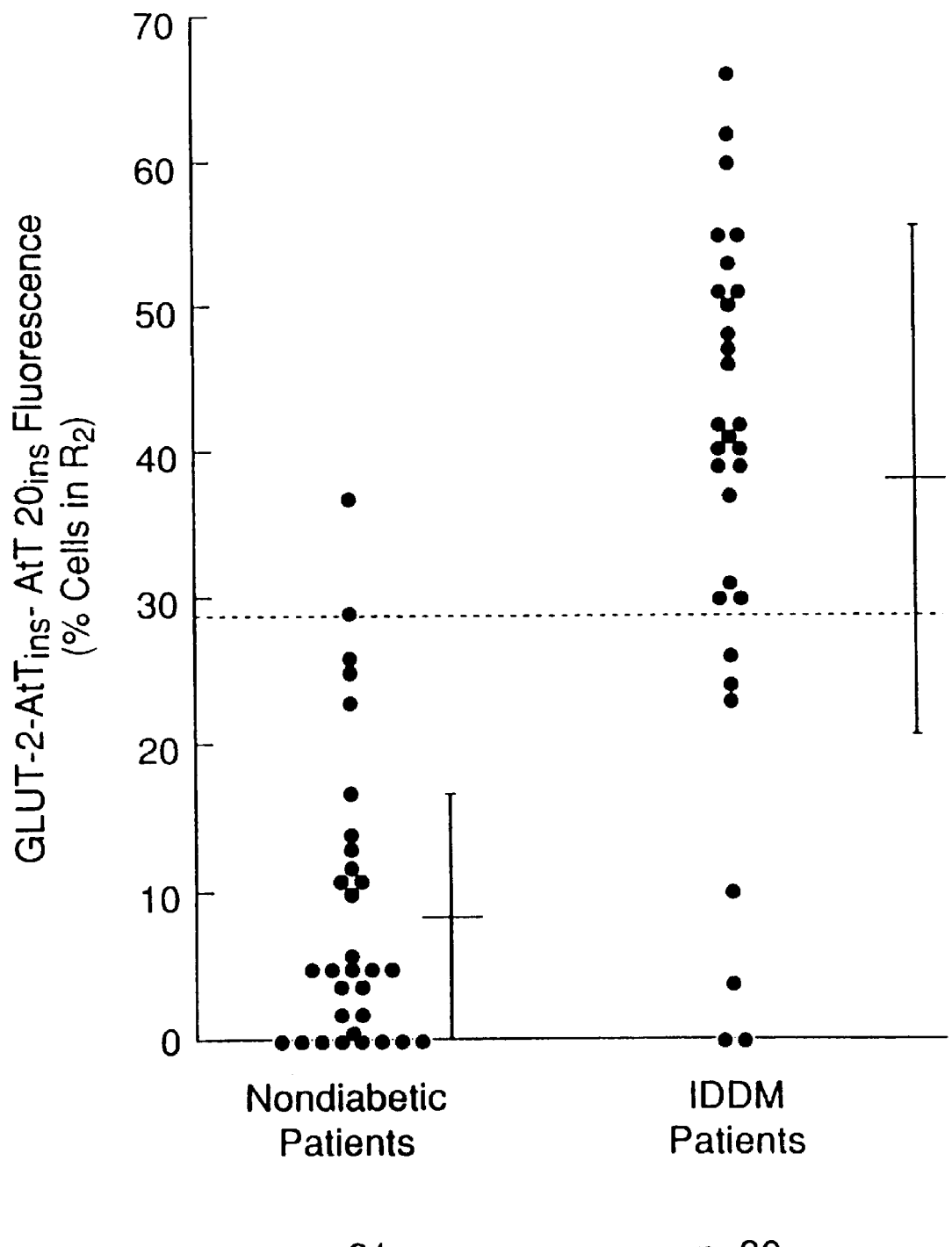
FIG. 8. Specific IgG binding to GLUT-2 expressing AtT20$_{ins}$ cells. Specific binding was determined by subtracting the percentage of cells found in R$_2$ using nontransfected atT20$_{ins}$ cells from cells found in R$_2$ using GLUT-2-expressing AtT20$_{ins}$ cells. Separation of the population of IDDM patients from the nondiabetic population is significant at p<0.0001.

As is discussed in greater detail in Example III, this flow cytometry-based immunofluorescence assay was found to be particularly useful in distinguishing the sera of patients with new-onset IDDM from non-diabetic subjects. It was found that 29 of 31 (94%) of the nondiabetic population were negative for IgG binding to GLUT-2 while 23 of 30 (77%) of sera from IDDM patients were positive (FIG. 8). Thus, 81% of negative results were from nondiabetic patients and 92% of positive results were from patients with IDDM (Table 2).

USE OF ENGINEERED CELLS IN THE IDENTIFICATION OF SPECIFIC EPITOPES

The present inventors have recently discovered that GLUT-1 transfected AtT-20ins cells do not discriminate diabetic from normal sera in FACS-based diagnostic tests, providing strong evidence that diabetic sera contain an antibody specific for the islet GLUT-2 glucose transporter. It is therefore envisioned that the artificial β-cells of the present invention will be of use in the identification of the specific epitope or segment of protein within GLUT-2 that is responsible for interacting with the antibody. Comparison of the GLUT-1 and GLUT-2 sequences reveals that the 2 putative membrane spanning regions in the two molecules are highly hydrophobic and of very similar sequence. These hydrophobic segments are connected by "loops" of amino acids that have much less sequence conservation (see Bell, et al., 1990 for review) In particular, GLUT-2 contains a very large extracellular loop between membrane spanning regions 1 and 2, while GLUT-1 contains a much smaller loop with little sequence homology to the GLUT-2 loop.

The inventors propose that construction of chimeric GLUT molecules in which individual or multiple "loop" regions are substituted could lead to identification of the specific epitope of GLUT-2 that reacts with diabetic sera. Thus, for example, the DNA encoding the large extracellular loop of GLUT-2 can be inserted in place of the small extracellular loop of GLUT-1 in the GLUT-1 cDNA sequence, and this chimeric molecule expressed in AtT-20ins cells. If the chimera reacts with diabetic serum (as the native GLUT-1 molecule does not), the added GLUT-2 extracellular loop would be the specific epitope. Once such an epitope is identified by the procedure outlined above, synthetic peptides corresponding to this region of the protein sequence can be produced and used to develop simpler diagnostic procedures. Examples would include a simple test in which the peptide epitope is reacted with test serum and the formation of an antibody/peptide complex is monitored by well established techniques such as ELISA or RIA.

INSULIN PRODUCTION FROM HIGH INSULIN-CONTENT ENGINEERED CELLS

GLUT-2 transfection is herein shown to cause an increase in intracellular insulin of approximately 5-fold in the AtT-20ins cell line, CGT-6. This finding demonstrates that batch extraction of insulin directly from these or related cells is an alternative strategy for isolation and purification of human insulin for use in IDDM therapy. CGT-6 cells contain approximately 1 mUnit/$10^6$ cells of human insulin when grown on gelatin beads in solution. The average IDDM patient requires approximately 30 Units of insulin per day for control of blood glucose levels. Cell densities of $5 \times 10^9$ cells/liter cell culture media are readily achieved in the current liquid culture configuration, meaning that 5 Units of insulin/liter can be produced. Much higher densities can be achieved using currently available commercial technology (e.g., that available from New Brunswick Scientific).

Furthermore, it is highly likely that the intracellular insulin content of the cells can be further increased by one of the following methods: 1) Retransfection of AtT-20ins cells with the Rous sarcoma virus/human proinsulin of cDNA plasmid that contains a resistance gene such as the neomycin resistance gene. The level of expression of a transfected gene appears to be dependent on the site of insertion of the plasmid in the chromosome. Thus, it is highly likely that higher levels of insulin expression will be achieved by simply reintroducing the plasmid and isolating new resistant clones. 2) Construction of plasmids in which human proinsulin cDNA expression is directed by alternate promoters. Examples include the CMV promoter, which was used to achieve very high levels of expression of GLUT-2 in the creation of the CGT-6 cell line in the inventor's laboratory, or 3) Amplification of the viral promoter/human proinsulin cDNA (Sambrook, et al., 1989) by cloning next to a resistance gene such as dihydrofolate reductase (DHFR), adenosine deaminase, or glutamine synthetase (Cockett, et al., 1990). Of these, DHFR is the most commonly used system, but is generally of limited usefulness in cell lines that have endogenous expression of DHFR (this is true of the AtT-20ins cell line). The glutamine synthetase system allows amplification of the gene of interest even in the presence of endogenous expression of glutamine synthetase.

Cells are stably transfected with a plasmid containing the transcription unit (i.e., viral promoter hooked to the human proinsulin gene) adjacent to the hamster glutamine synthetase coding sequences. Selection of clones and amplification of the integrated transcription unit/GS gene is then carried out by addition of methionine sulfoxide to the tissue culture media (Cockett, et al., 1990). Resulting clones contain greatly increased copy numbers of the transcription unit, by virtue of its association with the amplified glutamine synthetase gene. As a result, much greater quantities of insulin are produced by the recombinant cell, making it an even more viable source for human insulin production.

LIQUID CULTURE OF ENGINEERED CELLS FOR INSULIN PRODUCTION

As there has been little progress in developing new strategies for treating diabetes, therapy for diabetic patients is still centered around repeated self-injections of insulin. The methods employed for the production of human insulin to be used in this manner currently include either chemically completing purified recombinant insulin A and B chains, or purifying pig insulin from freshly isolated porcine pancreas or pancreatic islets. Both of these methods are technically difficult and laborious, and the latter is additionally complicated by the presence of many active proteases in the tissue of origin.

In considering the drawbacks of the methods currently employed for insulin production, the invention contemplates that correctly-folded human insulin could be produced relatively simply and rapidly using clonal β cells that secrete insulin in response to glucose.

The most appropriate method to accomplish this has been found by the inventors to be the perifusion of a column containing CTG-6 cells adhered to gelatin beads. Passing a glucose-containing buffer, such as KRS, 5 mM glucose, pH 7.4, over such a column of such artificial β cells has been found to stimulate the increased secretion of insulin into the surrounding media, which can then be collected and used as a starting material for the purification of recombinant insulin.

It is anticipated that purification of insulin from the perifusion media can be rapidly achieved by one or a combination of the following approaches: 1) Affinity chromatography, for example, passage of the insulin containing media over a column containing anti-insulin antibodies. After removal of non-insulin proteins and other impurities by washing of the column, insulin can be specifically eluted by using a buffer with an increased salt concentration or decreased pH. 2) Preparative high performance liquid chromatography. 3) Size selection by conventional size-exclusion column chromatography.

The following examples are included to demonstrate preferred embodiments of the invention. It should be appreciated by those of skill in the art that the techniques disclosed in the examples which follow represent laboratory techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

ENGINEERING OF GLUCOSE-STIMULATED INSULIN SECRETION IN NON-ISLET CELLS

A. Methods

1. AtT-20ins cell culture and tissue isolation

The AtT-20ins cells used were provided by Dr. Regis Kelly, University of California San Francisco, and were similar to the line that was originally described (Moore, et al., 1983) except that the Rous sarcoma virus long terminal repeat was substituted for the SV40 early gene promoter for directing insulin cDNA expression. The cells were grown in Dulbecco's modified Eagles' medium (DMEM), supplemented with 10% fetal calf serum, 100 μg/ml streptomycin, and 250 μg/ml neomycin. Anterior pituitary and liver samples were excised from normal ad-lib fed Wistar rats, and islets were isolated from groups of 10–20 animals as previously described (Johnson, et al., 1990a, 1990c) and pooled for RNA extraction or homogenization for glucose phosphorylation assays.

2. stable transfection of AtT-20ins cells with GLUT-2

The rat islet GLUT-2 cDNA (Johnson, et al., 1990s) was cloned into the vector pCB-7, a derivative of vector pCMV4 (Andersson, et al., 1989), immediately downstream of its cytomegalovirus (CMV) promoter. The cDNA was cleaved at its 3' end with Hind III, resulting in the removal of 635 base pairs of 3' untranslated region. AtT-20ins cells were transfected with this construct using electroporation. Cells were harvested from preconfluent plates by light trypsinization, washed twice in phosphate buffered saline, and resuspended at $3 \times 10^6$ cells/ml in a solution containing 20 mM Hepes (pH 7.05), 137 mM NaCl, 5 mM KCl, 0.7 mM $Na_2HP)_4$, 6 mM glucose, and 0.5 mg/ml salmon testis DNA. After equilibration of the cells to room temperature in electroporation cuvettes (Bio-Rad Labs; electrode gap width 0.4 cm), a single pulse was delivered using a capacitance setting of 960 μF and voltage settings between 0.2 and 0.3 kV. The cells remained in the buffer for five minutes and were then plated onto tissue culture dishes. Stable transfectants were selected with hygromycin, since the plasmid also contains a resistance gene for this drug. Four colonies were obtained and passaged several times in the presence of hygromycin to obtain a pure stock.

3. RNA blot hybridization analysis

RNA was prepared by guanidinium isothiocyanate extraction, resolved on a formaldehyde/agarose gel and transferred to a nylon membrane (Micron Separations Inc.) as previously described (Newgard, et al., 1986). Blots were hybridized sequentially with $^{32}P$ labeled antisense GLUT-2 or 18S rRNA probes, prepared as described (Chen, et al., 1990), with stripping of the blot between hybridizations by boiling in 0.1% SDS for 30 minutes.

4. Immunoblot analysis

Liver plasma membranes were prepared by the method of Axelrod and Pilch (1983) and only the light plasma membrane fraction was used. Islet and AtT-20ins cell membranes were prepared as previously described (Johnson, 1990b), except that the sucrose gradient was deleted and the homogenization buffer consisted of 50 mM Tris, pH 7.4, 5 mM EDTA, 0.1 mM p-chloromercurlbenzene sulfonate (PMSF), 10 mM benzamidine, and 1% Trasylol. The samples were transferred onto nitrocellulose and immunoblotted exactly as described (Hughes, et al., 1991; Quaade, et al., 1991), either with a 1:1000 dilution of the anti GLUT-2 polyclonal antiserum (Johnson, et al., 1990b), or with the diluted antiserum after 10 minutes of preincubation with an equal volume of a 1 mg/ml solution of the antigenic peptide dissolved in PBS. The second antibody was $^{125}I$-labeled goat anti-rabbit anti-IgG, and the resultant immune complexes were visualized by autoradiography.

5. GLUT-2 immunofluorescence in AtT-20ins cells

Parental AtT-20ins cells or transfected lines CGT-5 and CGT-6 were grown to a density of $5 \times 10^6$ cells per 100 mm dish and harvested by incubation at 37° C. with a solution of 0.02% EDTA in PBS. After three washes in DMEM containing 20 mM HEPES, approximately $1.5 \times 10^5$ cells were transferred onto 12 mm poly-L-lysine coated glass coverslips, to which they adhered during a 30 minute incubation at 37° C. The cells were then fixed with 3% paraformaldehyde in PBS for 30 minutes at room temperature, and incubated with 0.1M $NH_4Cl$ in phosphate buffered saline (PBS), pH 7.9 for 30 minutes. After 4 rinses with PBS, cells were permeabilized with 0.1% TRITON™ X-100 for 5 minutes, then rinsed 3 times with PBS. After a pre-incubation with 2% BSA, GLUT-2 antiserum (1:2500) was applied in the presence or absence of an equal volume of the antigenic peptide (1 mg/ml). Slides were incubated overnight, and excess antibody removed by washing 5 times with 0.1% BSA in 0.1M phosphate buffer, pH 7.9. Cells were then incubated with FITC-conjugated goat anti-rabbit IgG for two hours at 37° C. and washed sequentially with BSA/phosphate buffer and water. After application of coverslips, the slides were visualized by fluorescent light microscopy.

6. Glucose transport measurements

Cells were harvested by scraping with a rubber policeman, washed in Hanks balanced salt solution by centrifugation at 600×g, and resuspended in Dulbecco's modified Eagles's media with 10% fetal calf serum and 5 mM glucose. Cells were incubated at 37° C. for 30 minutes, washed, resuspended in phosphate buffered saline and assayed for 3-O-methyl glucose uptake as previously described (Johnson, et al., 1990c). Results were expressed as mmoles 3-O-methyl glucose uptake/min/liter cell space. Initial velocities of uptake were derived from duplicated measurements at 3, 6, and 15 seconds for each concentration of glucose with the transfected cell lines and 3, 15, and 30 seconds for the parental cell line (due to slower transport rate in these cells).

7. Glucose phosphorylation assays

Glucose phosphorylation and glucokinase activities were measured by conversion of U-$^{14}C$ glucose to U-$^{14}C$ glucose-6-phosphate, as previously described (Method "B" in Kuwajima, et al., 1986). Cultured cells or tissues were homogenized in 5 volumes of buffer containing 10 mM Tris, 1 mM EDTA, 1 mM $MgCl_2$, 150 mM KCl and 1 mM DTT, pH 7.2. The homogenate was cleared by centrifugation at 12,000×g and the supernatant used for assays of glucose phosphorylation. Reactions were carried out at 37° C. in a total volume of 150 μl, and initiated by addition of 10–30 μl of extract to a reaction mix containing 100 mM Tris, 5 mM ATP, 10 mM $MgCl_2$, 100 mM KCl, 1 mM DTT, pH 7.2, 15 or 50 mM glucose, and 6.2 μCi of U-$^{14}C$ glucose (300 mCi/mmol; New England Nuclear). In order to discriminate glucokinase and hexokinase activities, assays were performed in the presence and absence of 10 mM glucose-6-phosphate, which potently inhibits hexokinase but not glucokinase activity. Reactions were carried out for 90 minutes and terminated by addition of 50 μl of reaction mix to 100 μl of 3% methanol in 95% ethanol. An aliquot of this mixture was transferred to nitrocellulose filter circles (Grade NA 45, Schleicher & Schuell), which bind phosphosugars, and after air drying, washed extensively in water to remove labeled glucose. Radioactivity on the paper was then detected by liquid scintillation counting, and glucose phosphorylating activities are expressed in terms of the total protein content of the extracts.

8. Insulin secretion from AtT-20ins cells in response to secretagogues

Parental or GLUT-2 transfected lines CGT-5 and CGT-6 were removed from growth plates by light trypsinization and replanted in 6 well dishes (Costar) at a density of $5 \times 10^5$ cells per well. The cells were then grown for three days in culture media containing 1 mM (see above). On the third day, cells were washed twice for 10 minutes each in HEPES balanced salt solution containing 1% BSA (HBSS), but lacking glucose. Secretion experiments were initiated by addition of HBSS plus a range of glucose concentrations (0–20 mM) or in the presence of one of three non-glucose secretagogues, forskolin (0.5 µM), dibutyryl cAMP (5 mM), or isobutylmethylxanthine (IBMX, 0.1 mM), in the presence or absence of glucose. Cells were incubated with secretagogues for 3 hours, after which media was collected for insulin radioimmunoassay.

9. Assay of intracellular insulin

Cells were collected in 1 ml of 5M acetic acid, lysed by three cycles of freeze-thawing, and lyophilized. The dried lysate was then reconstituted in 5 ml of insulin assay buffer (50 mM $NaH_2PO_4$, 0.1% BSA, 0.25% EDTA, 1% aprotinin, pH 7.1) and aliquots were assayed for insulin by radioimmunoassay.

B. Results

1. Expression of GLUT-2 mRNA in transfected AtT-20ins cells

Expression of GLUT-2 mRNA was evaluated by blot hybridization analysis of AtT-20ins cells, either transfected or untransfected with a cytomegalovirus (CMV) promoter/GLUT-2 hybrid gene, and in extracts of rat liver, islets of Langerhans, and anterior pituitary tissues. The radiolabeled GLUT-2 antisense RNA probe (Johnson, et al., 1990a; Chen, et al., 1990) was hybridized to a blot containing equal amounts of RNA from four GLUT-2 transfected AtT-20ins cell lines (CGT-1, CGT-2, CGT-5, CGT-6), untransfected AtT-20ins cells, and the three primary tissues (FIG. 1). Steady state levels of GLUT-2 MRNA were highest in CGT-5 and CGT-6; the former contained approximately half as much and the latter an equal amount of GLUT-2 MRNA as rat islets, and they contained 10 and 16 times as much, respectively, as rat liver, measured by densitometric scanning and normalization to the signal obtained with an 18SrRNA probe. The transfected lines contained a smaller GLUT-2 transcript than liver or islets (2.2 versus 2.8 kb) because 635 base pairs of the 3' untranslated region were removed in the course of cloning the GLUT-2 cDNA into the pCB-7 vector. Lines CGT-1 and CGT-2 exhibited less active expression of GLUT-2. Untransfected AtT-20ins cells and primary anterior pituitary cells did not contain detectable amounts of GLUT-2 mRNA, consistent with previous studies (Hughes, et al., 1991).

2. Expression of GLUT-2 protein in tissues and cell lines

In order to evaluate the levels and molecular status of the expressed GLUT-2 protein in transfected AtT-20ins cells, we resolved crude membrane fractions by SDS/PAGE, transferred the proteins to nitrocellulose, and detected GLUT-2 protein with an antibody raised against its C-terminal hexadecapeptide sequence (Johnson, et al., 1990b). The antibody recognized two distinct bands in liver and islets, with apparent molecular weights of 70 and 52 kd in liver and slightly different sizes of 72 and 56 kd in islets (FIG. 2, left). Consistent with the RNA blot hybridization data, untransfected AtT-20ins cells were found to lack GLUT-2 protein, while a single intense band of approximately 70 kd was observed in extracts from either of the transfected lines CGT-5 and CGT-6. The specificity of the antibody is demonstrated by the fact that all bands were blocked by preincubation of the antibody with the antigenic peptide (FIG. 2, right). Thorens, et al. (1988) have previously reported that a similar anti-peptide antibody recognizes GLUT-2 proteins of distinct molecular weights in liver (53 kd) and islets (55 kd), despite the fact that the cDNA sequences for GLUT-2 are identical in liver and islets in both rat (Johnson, et al., 1990a) and man (Permutt, et al., 1989). They did not report on the larger bands shown herein, possibly because of differences in the protocols used for membrane preparation.

3. Immunocytochemistry of GLUT-2 in transfected AtT-20ins cells

Expression of GLUT-2 protein in transfected AtT-20ins cells was studied by immunofluorescent staining techniques, using an antibody raised against the C-terminal hexadecapeptide of GLUT-2 (Johnson, et al., 1990b). In the lines with highest GLUT-2 mRNA levels (CGT-5 and CGT-6), abundant GLUT-2 immunofluorescence was detected at the cell membrane as well as some intracellular signal that was mostly polarized to regions of cell-cell contact. The signal was blocked by preincubation of the antibody with the antigenic peptide and was not seen in untransfected cells or in cells transfected with the vector lacking the GLUT-2 insert. Expression of GLUT-2 protein in transfected AtT-20ins cells and its absence in the untransfected parental line was confirmed by immunoblot analysis. Thus, AtT-20ins cells and its absence in the untransfected parental line was confirmed by immunoblot analysis. Thus, AtT-20ins cells not only have the capacity to produce GLUT-2 mRNA and protein but also sort the protein to the cell membrane, as occurs in both islets and liver (Thorens, et al., 1988; Orci, et al., 1989; Tal, et al., 1990; Orci, et al., 1990). Preferential expression at regions of cell-cell contact is in keeping with a recent report (Orci, et al., 1989) showing that GLUT-2 expression in islet β-cells is not homogenous and is most abundant in regions of membrane enriched in microvilli and facing adjacent endocrine cells, as opposed to regions facing capillaries or empty spaces between cells. The functional significance of this phenomenon is currently not understood.

4. Glucose transport measurements in parental and GLUT-2 expression AtT-20ins cells The GLUT-2 cDNA has been cloned from both liver (Thorens, et al., 1988) and islets (Permutt, et al., 1989; Johnson, et al., 1990a), two tissues with high Km glucose transport activity. Although the cDNA has been expressed in bacteria (Thorens, et al., 1988) and oocytes (Permutt, et al., 1989), these systems have not been used for kinetic studies. Thus, direct evidence that the GLUT-2 cDNA encodes a protein that confers the high Km glucose transport activity has not been presented to date.

Figure 3A:
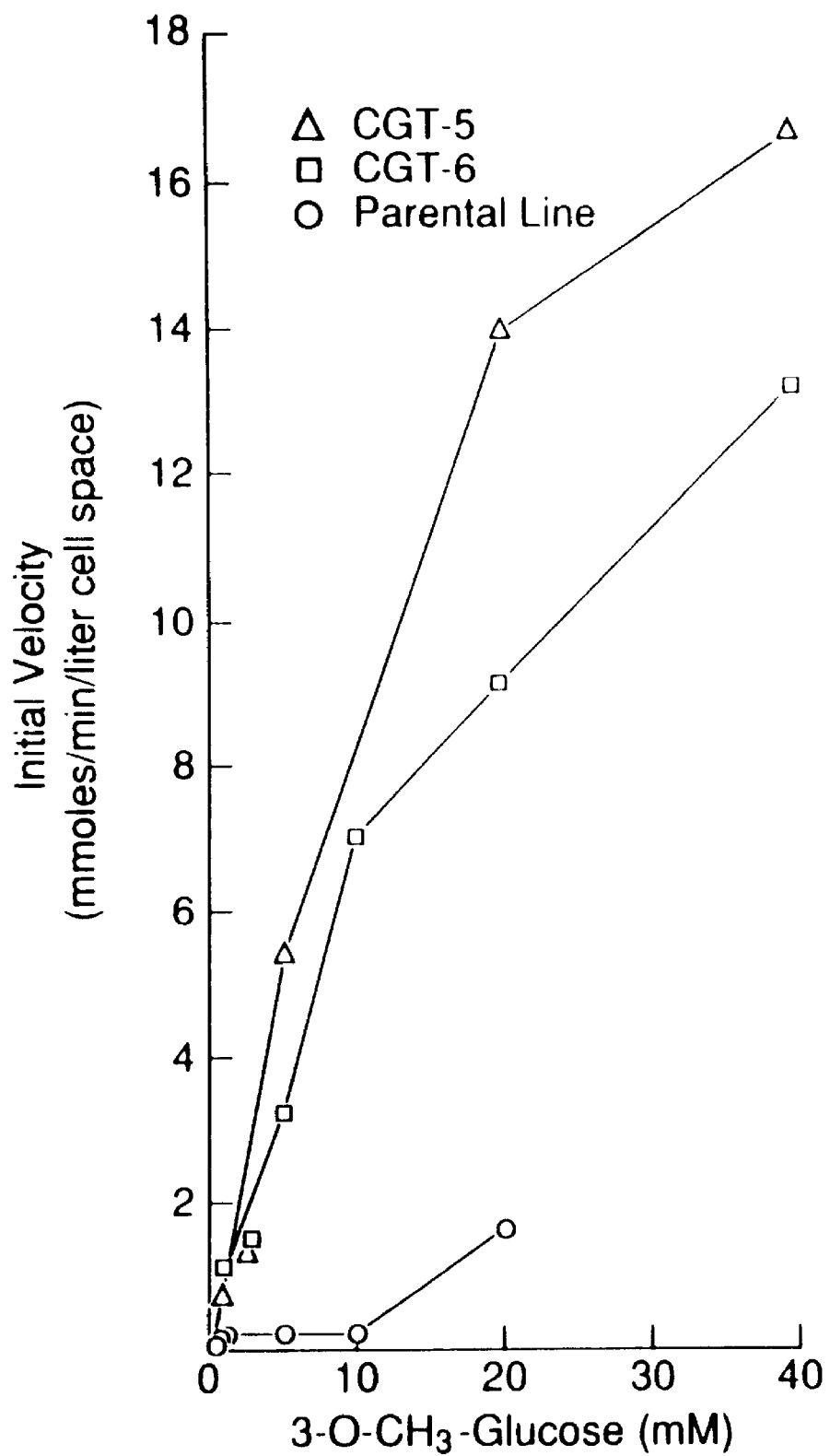
FIG. 3A, FIG. 3B and FIG. 3C. Glucose transport into AtT-20ins cells.
Figure 3B:
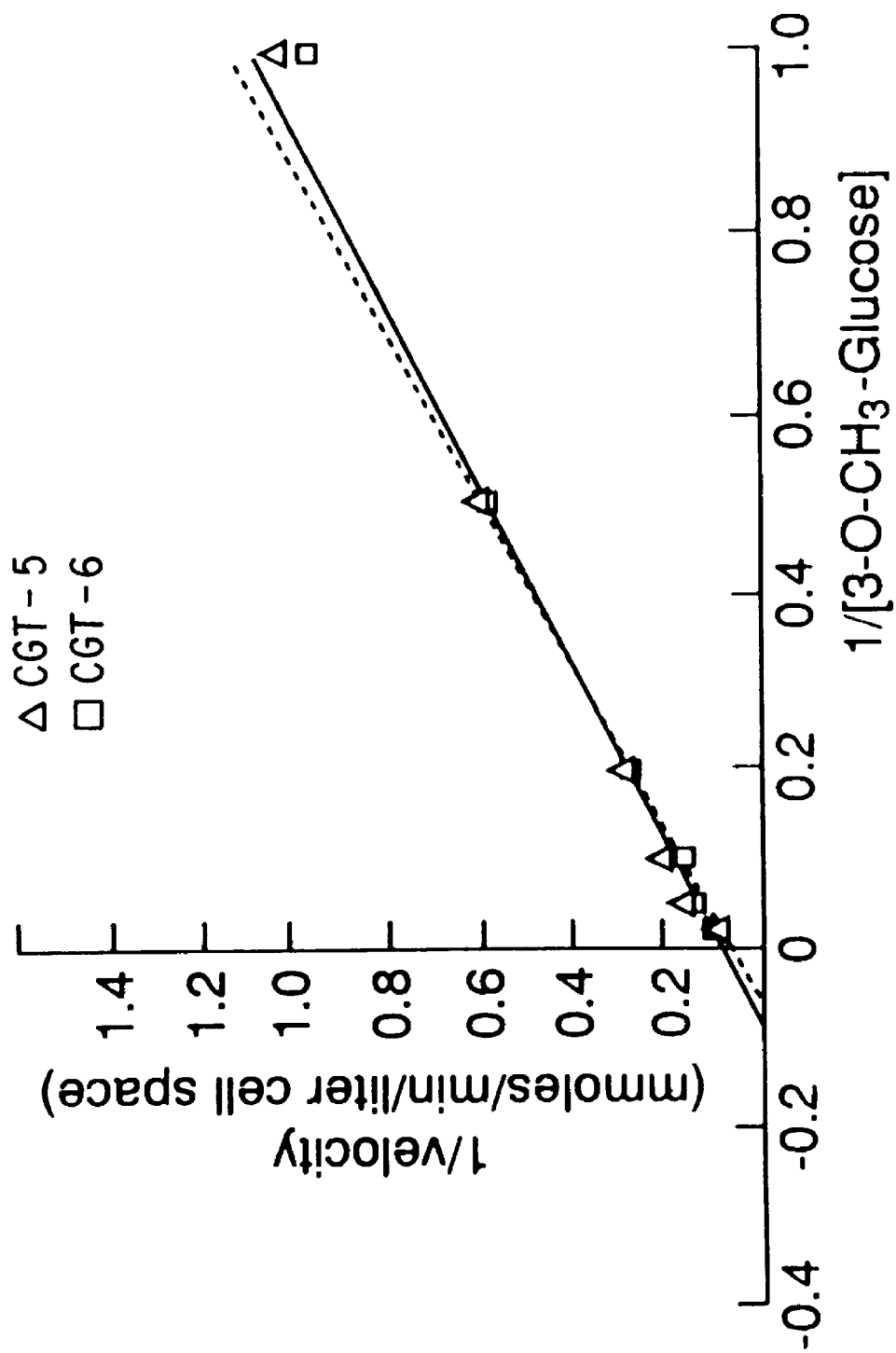
Figure 3C:
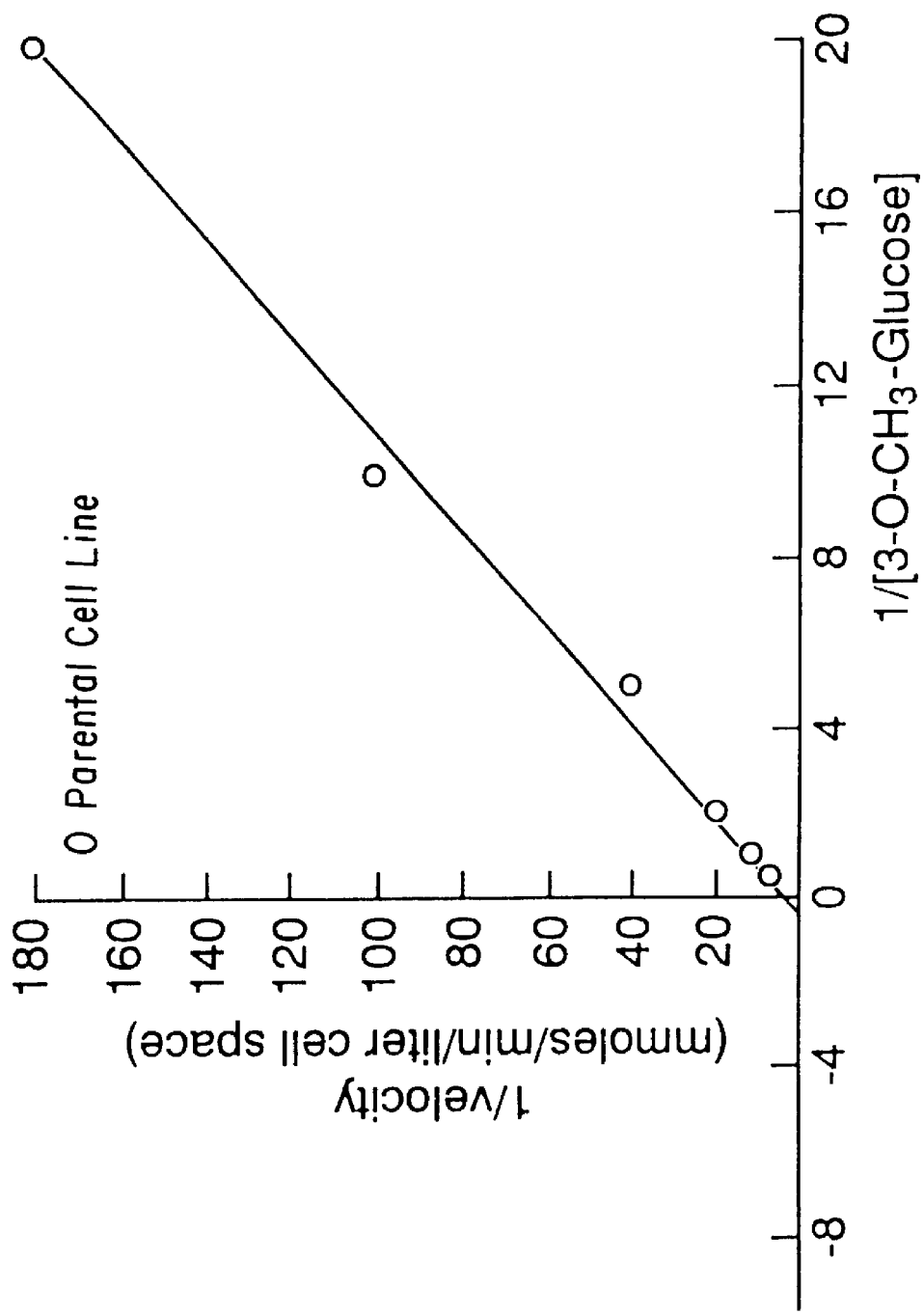

Dramatic differences in glucose transport kinetics were found between transfected and untransfected AtT-20ins cells. FIG. 3A shows a plot of the concentration dependence of glucose uptake in the AtT-20ins cell lines, and demonstrates the dramatically increased rates of glucose transport in lines CGT-5 and CGT-6 relative to the untransfected (parental) AtT-20ins cells. Lineweaver-Burke analysis of the data showed that the CGT-5 and CGT-6 lines had apparent Kms for glucose of 16 and 17 mM and Vmax values of 25 and 17 mmoles/min/liter cell space, respectively (FIG. 3B). In contrast, the untransfected parental AtT-20ins line had an apparent Km for glucose of 2 mM and a Vmax of 0.5 mmoles/min/liter cell space (FIG. 3C), consistent with its expression of the GLUT-1 mRNA (Hughes, et al., 1991), which encodes the low Km glucose transporter found in most clonal cell lines (Flier, et al., 1987; Birnbaum, et al., 1987). The transfected AtT-20ins cells have glucose transport kinetics that are remarkably similar to isolated, dispersed islets of Langerhans, which have a Km of 18 mM for glucose and a Vmax of 24 mmoles/min/liter cell space (Johnson, et al., 1990a). Thus, the GLUT-2 cDNA clearly encodes the protein responsible for the high Km glucose transport activity in islets and liver, and is capable of transferring this activity into the AtT-20ins cell line.

5. Glucose-stimulated insulin secretion from AtT-20ins cells

Figure 4A:
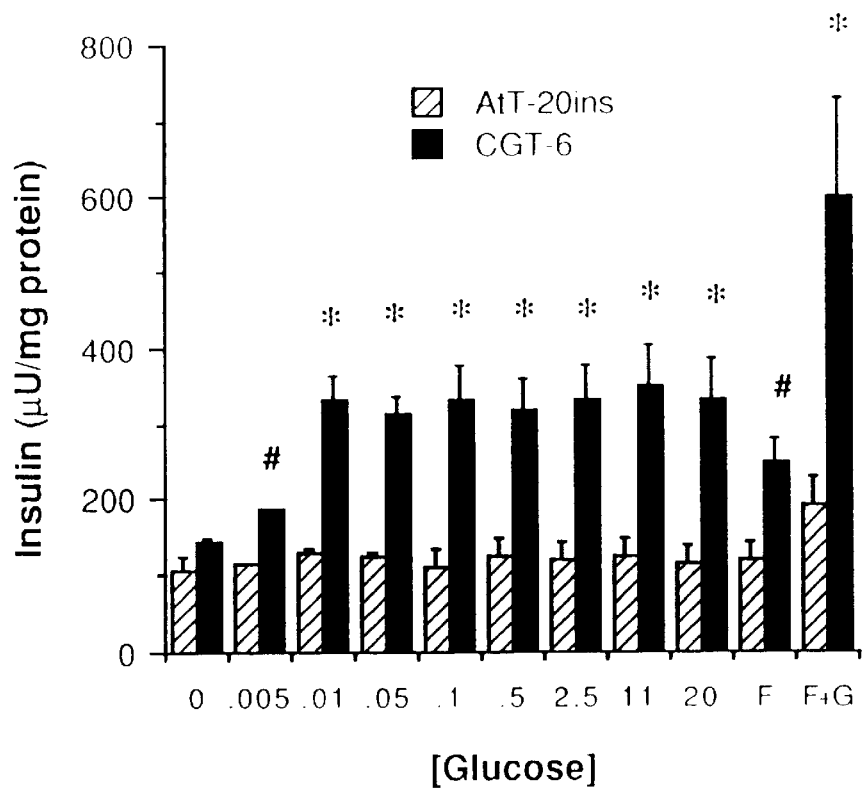
FIG. 4A and FIG. 4B. Insulin release for AtT-20ins cells in response to glucose, and glucose potentiation of forskolin induced secretion.

Insulin secretion from GLUT-2 transfected and untransfected cells was measured over a range of glucose concentrations from 0–20 mM. FIG. 4A compares glucose-stimulated insulin release from AtT-20ins cells and CGT-6 cells, expressed as mU insulin released/mg total cellular protein. Consistent with previous results (Hughes, et al., 1991), glucose had no significant effect on insulin release from parental AtT-20ins cells. AtT-20ins cells transfected with the pCB7 vector lacking a GLUT-2 insert were also found to be unresponsive to glucose. GLUT-2 transfected cells, in contrast, are clearly glucose responsive (data are shown for line CGT-6 only; results for line CGT-5 were qualitatively identical). A submaximal but statistically significant (p=0.002) increase in insulin release relative to insulin release at 0mM glucose was observed at the lowest concentration of glucose studied (5 $\mu$M); maximal stimulation of approximately 2.5-fold was observed at all higher concentrations over the range 10 $\mu$m–20 mM (p$\leq$0.001). It is highly unlikely that these results can be attributed to clonal selection of glucose responsive subpopulations of the parental AtT-20ins cells, since cells transfected with vector lacking GLUT-2 failed to respond, while two independent GLUT-2 expressing lines (CGT-5 and CGT-6) gained glucose sensing.

Figure 4B:
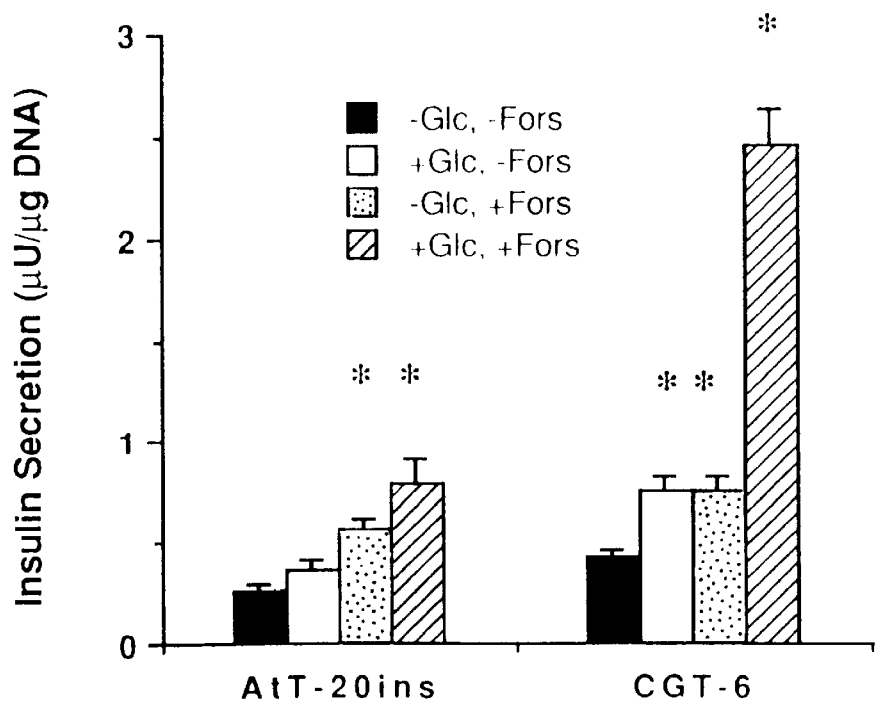

In normal islets, glucose potentiates the insulin secretory response to various $\beta$-cell secretagogues, including agents that increase intracellular cAMP levels (Ullrich and Wollheim, 1984; Malaisse, et al., 1984). The potentiating effect of glucose on insulin secretion in the presence of forskolin, dibutyryl cAMP, and IBMX was therefore studied. Glucose had a modest stimulatory effect on forskolin stimulated insulin release from parental AtT-20ins cells, expressing the data either as insulin release/mg cellular protein (FIG. 4A) or as insulin release/mg cellular DNA (FIG. 4B). In contrast, glucose had a powerful potentiating effect on forskolin stimulated insulin release from transfected CGT-6 cells. The response was unchanged by glucose concentration over the range of 1–5 mM, and similar potentiating effects of glucose on dibutryl cAMP and IBMX induced secretion were also observed.

Figure 9:
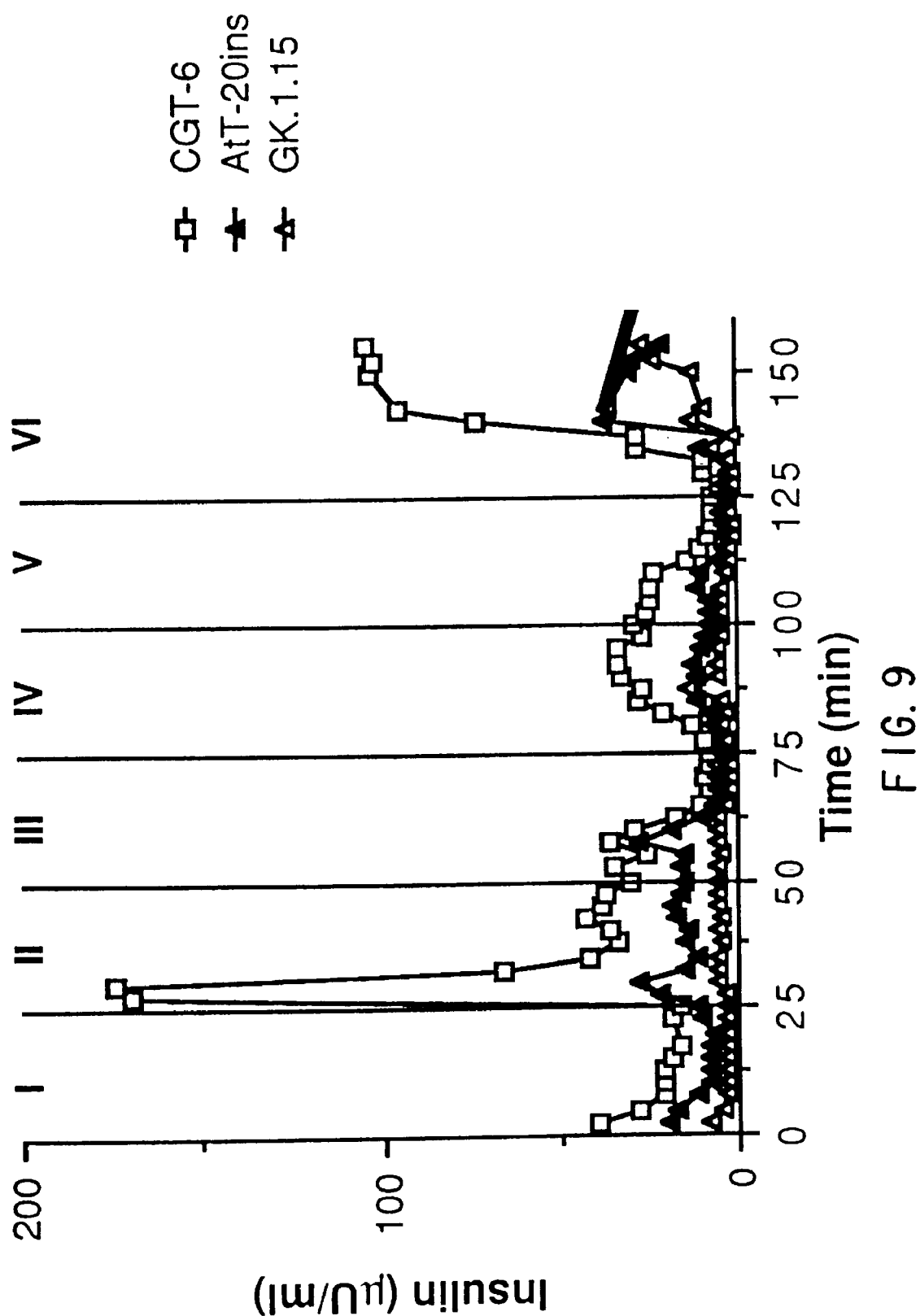
FIG. 9. Insulin release from GLUT-1 versus GLUT-2 transfected AtT-20ins cells during perifusion with glucose and forskolin. Approximately 50×10$^6$ cells were perifused at a flow rate of 0.5 ml/minute with HBBS buffer containing 0 mM glucose (phases I, III, and V), 5 mM glucose (phases II and IV), or 5 mM glucose+0.5 μM forskolin (phase VI). Effluent media samples were collected in 1.25 ml aliquots (every 2.5 minutes) and assayed for insulin by radioimmunoassay. CGT-6, GLUT-2 transfected AtT-20ins cells; GT1-15, GLUT-1 transfected AtT-20ins cells; AtT-20ins, parental cell line. The results of one typical experiment are shown.

Insulin secretion experiments involved static incubation of cells with the secretagogue for three hours, and thus provided little information about the dynamics of insulin release. The inventors succeeded in growing the parental and transfected AtT-20ins cell lines on gelatin beads in liquid culture, thus allowing their secretory properties to be studies by perfusion with glucose containing media. As shown in FIG. 9, cells grown in this configuration released insulin within minutes of glucose stimulation. Furthermore, the insulin secretory response exhibits a first intense and a second less intense but sustained phase, as is characteristic of normal $\beta$ cells.

6. Insulin Content of Native and Engineered AtT-20ins cells

A remarkable finding of this study is that transfection of AtT-20ins cells with the GLUT-2 cDNA results in a substantial increase in intracellular insulin content, despite the fact that insulin gene expression is driven by the glucose insensitive Rous sarcoma virus long-terminal repeat enhancer/promoter in these cells. Native AtT-20ins cells and the GLUT-2 transfected CGT-6 cells were grown for 3 days in media supplemented with low (1 mM) or high (25 mM) glucose. The CGT-6 cells were found to contain 3.6-fold and 5.4-fold more insulin than the AtT-20ins cells when studied at low and high glucose, respectively (p<0.001 for both comparisons). Furthermore, insulin content was approximately double in the CGT-6 cells grown at high glucose compared with the same cells grown at low glucose (p<0.001); In contrast, in the untransfected AtT-20ins cells, high glucose caused only a 20% increase in insulin content.

7. Glucose phosphorylation in AtT-20ins cells

AtT-20ins cells were transfected with GLUT-2 secrete insulin at glucose concentrations that are substimulatory for islets. The enhanced sensitivity to glucose is not explained by the kinetics of glucose transport, since both the CGT-5 and CGT-6 lines transport glucose with a velocity and concentration dependence that is virtually identical to islets. Alternatively, stimulation of insulin secretion al low glucose concentrations might be explained by differential regulation of glucose phosphorylation in AtT-20ins cells relative to $\beta$-cells. The ratio of hexokinase:glucokinase activity in these cells was therefore compared with activities found in normal islets of Langerhans and liver. Studies from this and other laboratories (Iynedjiian, et al., 1989; Magnuson and Shelton, 1989; Newgard, et al., 1990; Hughes, et al., 1991) have shown that the single glucokinase gene is alternatively regulated and processed in liver and islets, resulting in distinct transcripts that predict proteins with unique N-termini; the Km for glucose of both isoforms is in the range of 8–10 mM. AtT-20ins cells express the islet isoform of glucokinase (Hughes, et al., 1991).

A radioisotopic glucose phosphorylation assay was performed (Method "B" in Kuwajima, et al., 1986) that allows discrimination of glucokinase and hexokinase activities when performed in the presence and absence of 10 mM glucose-6-phosphate, since this metabolite is a potent inhibitor of hexokinase, but not glucokinase (Wilson, 1984). As shown in Table 1, total glucose phosphorylating capacity and glucokinase activity are not significantly different in transfected (line CGT-6) versus untransfected (parental) AtT-20ins cells. Both lines have a total glucose phosphorylating capacity that is similar to that in liver and islets. However, glucokinase activity in AtT-20ins cells is only 32% of the glucokinase activity in islets and 10% of that in liver. Moreover, glucokinase represents only 9% of the total glucose phosphorylating activity of AtT-20ins cells (the remaining 91% is presumably due to hexokinase activity), as compared to 24% in normal islets and 86% in normal liver. The altered hexokinase:glucokinase ratio in AtT-20ins cells may result in low Km glucose metabolism that accounts for the insulin secretory response at low glucose concentrations.

TABLE 1

Glucose Phosphorylating Activities in Tissues and Cell Lines.

| Cell Type | Total Glucose* Phosphorylation (U/gram protein) | Glucokinase# (U/gram protein) | Glucokinase (% of total) |
|---|---|---|---|
| AtT-20 ins (parental) | 9.19 ± 0.27 | 0.63 ± 0.06[a] 0.43 ± 0.08[b] | 6.8% |
| AtT-20 ins (line CGT-6) | 8.09 ± 0.20 | 0.86 ± 0.18[a] | 10.6% |
| Islet | 9.61 ± 2.10 | 2.31 ± 0.35[a] | 24.0% |
| Liver | 8.42 ± 1.09 | 7.19 ± 1.31[a] | 85.4% |

*Total glucose phosphorylation was measured in 14,000 × g supernatant of crude homogenates, at 50 mM glucose, using an assay that monitors $^{14}$C glucose conversion to $^{14}$C glucose-6-phosphate ("Method B" in Kuwajima, et al., 1986).

TABLE 1-continued

Glucose Phosphorylating Activities in Tissues and Cell Lines.

| Cell Type | Total Glucose* Phosphorylation (U/gram protein) | Glucokinase# (U/gram protein) | Glucokinase (% of total) |
| --- | --- | --- | --- |

Glucokinase activity was determined with the same assay as used for total glucose phosphorylation at 50 ($^a$) or 15 ($^b$) mM glucose, except in the presence of 10 mM glucose-6-phosphate to inhibit hexokinase. Values represent the means ± SEM for 3 independent determinations for liver and islets and 4 independent determinations for untransfected (parental) and GLUT-2 transfected (line CGT-6) AtT-20 ins cells.

EXAMPLE II

DIAGNOSIS OF IDDM

A. Methods

1. Direct inspection of immunoreactive cells by fluorescence microscopy

Parental and engineered AtT-20ins cells are grown to a density of 5×10$^6$ cells per 100 mm dish and harvested by incubation at 37° C. with a solution of 0.02% EDTA in phosphate buffered saline (PBS). After washing the cells in DMEM media containing 20 mM Hepes, approximately 1.5× 10$^5$ cells are transferred onto 12 mm poly-L-lysine coated glass coverslips, to which they adhere during a 30 minute incubation at 37° C. The cells are then fixed for 30 minutes with varying amounts (0.5–3.0%) of paraformaldehyde, depending on the extent of fixation that is desired. For studies with anti-GLUT-2 antibodies or serum, the inventors have found a light fixation (0.5% paraformaldehyde) to be most appropriate. After preincubation with 2% BSA, a serum sample (usually diluted 1:1 in BSA) is added to the sample in sufficient volume to cover the cells. As a positive control, an antibody (designated X617) raised against the unique extracellular loop peptide of the rat GLUT-2 transporter is used, diluted 1:100 in PBS (the antibody is raised against a peptide with sequence DAWEEETEGSAHIV (SEQ ID NO. 1), as found at amino acids 64–77 of the rat GLUT-2 primary structure).

Slides are incubated overnight with serum or antibody, and excess antibody is removed by washing with 0.1% BSA in 0.1M phosphate buffer, pH 7.9. Cells are then incubated with FITC-conjugated goat anti-human IgG (in the case of human serum samples) or FITC-conjugated goat anti-rabbit IgG (in the case of antibody X617, which was raised in rabbits). After application of coverslips, the slides are visualized by fluorescent light microscopy. A test is scored as positive if for a particular serum sample, a clear fluorescent signal is seen at the membrane surface of GLUT-2 expressing AtT-20ins cells but not in parental AtT-20ins cells. A positive response with antibody X617 further proves that the GLUT-2 protein is expressed in proper orientation and that epitopes that are expected to reside at the cell surface are indeed recognizable.

2. Use of a fluorescence activated cell sorter (FACS) to score immune complex formation Cells are prepared for FACS analysis essentially as described for the microscope slide approach except that incubations are done with cells in suspension rather than attached to microscope slides. Briefly, near-confluent tissue culture plates containing parental AtT-20ins cells or GLUT-2 expressing CGT-6 cells are washed with PBS, and then exposed to 0.02% EDTA for 15 minutes at 37° C. to dislodge cells from the plate. The dispersed cells are washed with culture media followed by PBS and used as intact, live cells or fixed gently in 0.5% paraformaldehyde/PBS for 15 minutes at room temperature. The live or fixed cells are then incubated in 100 μl of patient serum: PBS in a ratio of 1:1, with 0.002% EDTA added to keep the cells dispersed. After a one hour incubation at 4° C., the cells are washed 3 times with PBS and incubated with anti-human IgG or anti-human globulin fraction labeled with phycoerythrin for 1 hour at 4° C. Subsequently, the cells are washed with PBS and run through a flow cytometer in the red channel. Phycoerythrin is chosen as the fluorescent marker because we found the AtT-20ins cells have a natural fluorescence in the green channel that is used for FITC-labeled antibodies.

B. Results

1. Microscope slide technique

Use of the antibody raised against-the external loop peptide of GLUT-2 in the inventor's laboratory (X617) results in a clear fluorescent staining at the surface of engineered AtT-20ins cells that express GLUT-2, but gives no such signal in parental cells that have not been engineered for GLUT-2 expression. Furthermore, the signal in GLUT-2 transfected cells can be blocked by preincubation of antibody X617 with the peptide to which it was raised. These results indicate that formation of an immune complex with an external (extracellular) epitope of the GLUT-2 protein can occur and is readily detectable. In preliminary studies with sera isolated from new-onset Type I diabetic patients (ranging in age from 10–20 years old), and age matched normal controls, the diabetic sera, but not the normal sera show a greater immunoreactivity against the GLUT-2 transfected cells relative to the untransfected controls.

2. FACS technique

Figure 5A:
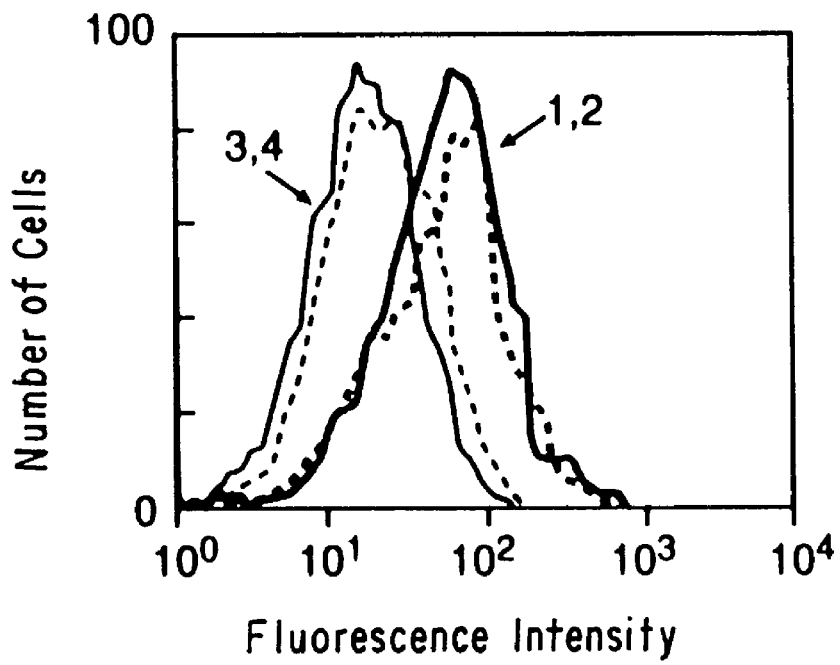
FIG. 5A and FIG. 5B. The utility of the FACS method for detecting the presence of a specific immune complex.
Figure 5B:
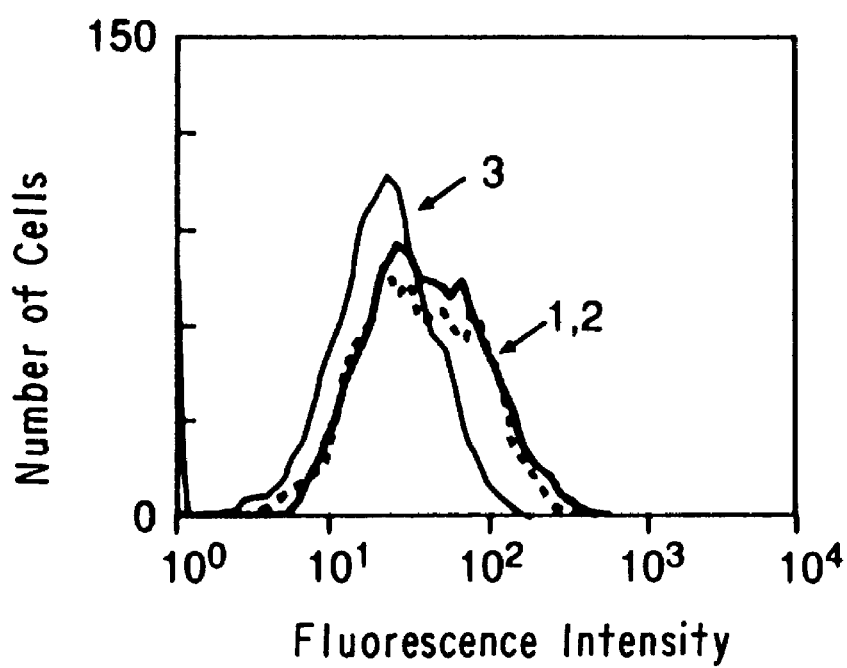

The FACS method was found to be appropriate for detecting the presence of a specific immune complex (FIG. 5A and FIG. 5B). Graphs 1 and 2 of FIG. 5A were derived by treatment of GLUT-2 expressing AtT-20ins cells with the anti-GLUT-2 antibody X617 and treatment with anti-rabbit IgG second antibody labeled with phycoerythrin. Graphs 3 and 4 represent cells incubated with antibody X617 after it had been preincubated with GLUT-2 expressing AtT-20ins cells. The cells are loaded into the FACS, which passes the cells one-by-one past a light source set at a wavelength that will excite the fluorescent marker of the second antibody. The cells then pass a detector which measures the fluorescence emission from the cells. Data are plotted as a histogram of fluorescence intensity. As can be seen, curves 1 and 2 are shifted to the right relative to curves 3 and 4, indicating a greater fluorescence intensity in those cells. A similar experiment was performed with parental AtT-20 ins cells not expressing GLUT-2 (FIG. 5B). In these cells, no difference is seen between the naked antibody and antibody preabsorbed with GLUT-2 expressing cells. Taken together, these data serve to validate the technique, in that a specific response can be measured to an antibody known to react with an extracellular domain of GLUT-2.

Figure 6A:
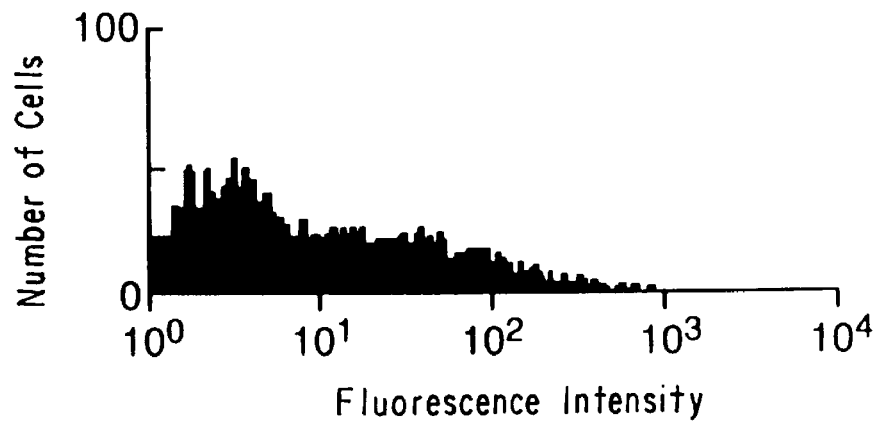
FIG. 6A: Graphs 1 and 2 are derived by treatment of GLUT-2 expressing AtT-20ins cells with the anti-GLUT-2 antibody X617 and treatment with anti-rabbit IgG second antibody labeled with phycoerythrin. Graphs 3 and 4 represent cells incubated with antibody X617 after it had been preincubated with GLUT-2 expressing AtT-20ins cells.
Figure 6B:
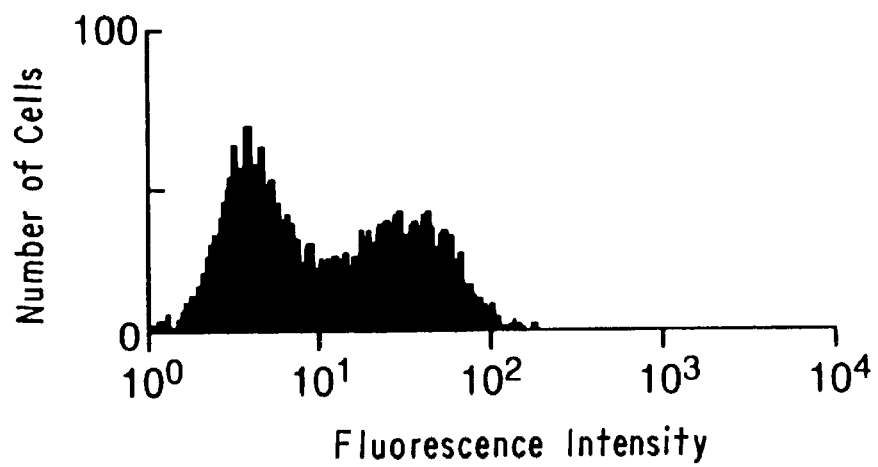
Figure 6C:
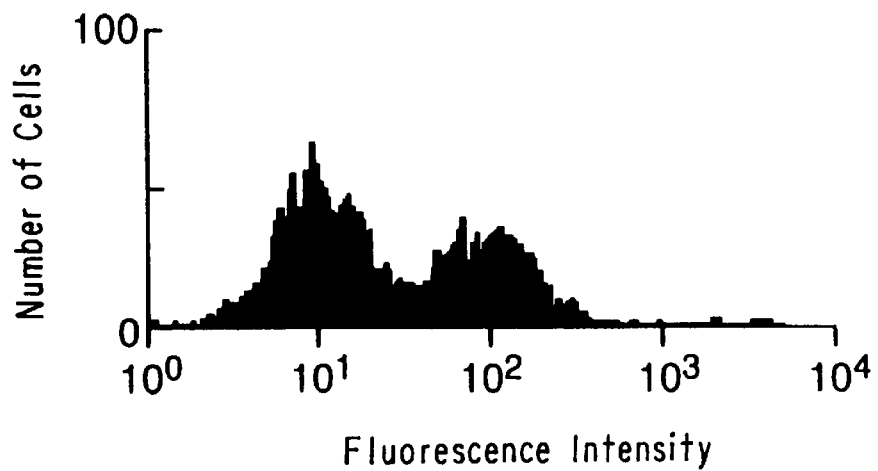

This method was used in the preliminary analysis of serum from a diabetic patient (FIG. 6A, FIG. 6B and FIG. 6C). FIG. 6A shows the fluorescence spectrum of GLUT-2 transfected AtT-20ins cells incubated with the second antibody (phycoerythrin labeled anti-human globulin) alone. In FIG. 6B, the GLUT-2 transfected cells have been incubated with serum isolated from a normal patient, resulting in a shift in the fluorescence intensity relative to the control in FIG. 6A. In FIG. 6C, cells are incubated with serum from a patient with new-onset Type I diabetes. Importantly, this serum causes a much more pronounced rightward shift in fluorescence relative to the normal or nonserum controls. The sample shown is representative of most other diabetic and normal sera assayed to date.

EXAMPLE III

INTERACTIONS OF SERA FROM DIABETIC PATIENTS

WITH ISLET CELLS AND ENGINEERED AtT20$_{ins}$ CELLS

The following example is directed to an analysis of serum samples from diabetic patients and non-diabetic subjects. In particular, the interactions of purified IgG samples with rat islet cells and engineered AtT20$_{ins}$ cells was investigated using both binding assays and assays based on the inhibition of glucose uptake. The following results demonstrate the usefulness of such analyses in diagnostic and prognostic tests.

A. Immunofluorescence/Flow Cytometric Methods

AtT20$_{ins}$ cells and GLUT-2-expressing AtT20$_{ins}$ cells were harvested by removal of cells from plates with a rubber policeman in Dulbecco's phosphate-buffered saline, pH 7.6. Following two washes in Dulbecco's phosphate-buffered saline by sedimentation at 500×g for 30 seconds at room temperature, the cells were divided into 1.5 ml microfuge tubes at a density of approximately $10^5$ cells per tube. Cells were incubated for 1 hour at 4° C. in 150 µg of patient sera with occasional agitation. The cells were then washed twice by centrifugation at 500×g for 30 seconds in Dulbecco's phosphate-buffered saline pH 7.6 and resuspended in R-phycoerythrin-labeled goat antihuman, heavy chain-specific IgG (R-PEAb) (Fisher Scientific) and incubated for 1 hour at 4° C. with occasional shaking. Following an additional two washes by centrifugation at 500×g for 30 seconds in Dulbecco's phosphate-buffered saline, pH 7.6, the cells were resuspended in 500 µl of Dulbecco's phosphate-buffered saline, pH 7.6, and analyzed for IgG. binding using flow cytometry.

Flow cytometry was performed on a FACScan (Becton Dickinson) flow cytometer. Forward scatter threshold was set at 100 using the E-01 forward scatter detector. Linear amplifier gains were 6.18 for forward scatter and 1.22 for 90° angle light scatter with a photomultiplier setting of 274 volts. Forward and 90° angle light scatter were read on linear scale and fluorescence measurements were made on logarithmic scale. Setting adjustments were made by using a sample of unstained cells and increasing the photomultiplier voltage so that events were on-scale during observation of 530±15 nm (FLI) histogram. A sample of cells stained only with R-phycoerythrin-labeled goat antihuman IgG (R-PEAb) was then used to adjust the photomultiplier voltage so that events were on-scale during measurement of a 575±13 nm (FL2) histogram. A control specimen was then used to adjust the FL2 photomultiplier tube voltage such that FL2 histogram events remain minimally on scale. The FL2-FL1 compensation was adjusted to minimize fluorescence overlap and for these cells a setting of 45.9% was used. Acquisition of $10^4$ events per specimen were required and data were stored on floppy discs for analysis.

B. Results

1. Effects of IgG from Diabetic Patients and Nondiabetic Subjects on 3-O-Methyl-β-D-Glucose Uptake by Islet Cells and GLUT-2-Expressing and GLUT-1-Expressing AtT20$_{ins}$ Cells The following assays were performed to investigate the effects of human IgG on glucose uptake by intact cells. The assays were performed as described by Johnson and Unger, PCT Patent Application WO 91/13361, incorporated herein by reference.

Examination of the effects of purified IgG from 7 patients with new-onset IDDM and 6 nondiabetic individuals revealed that 3-O-methyl-β-D-glucose uptake by rat islet cells was significantly inhibited in the presence of IgG from patients with IDDM (FIG. 7A, FIG. 7B and FIG. 7C). Initial rates of uptake averaged 15 mmoles 3-O-methyl-glucose/min/liter islet cell space in the presence of IgG from nondiabetic patient sera versus 9 mmoles 3-O-methyl-glucose/min/liter islet cell space in the presence of IgG from sera of patients with IDDM (p<0.05). These rates translate into a 40% inhibition of glucose transport in the presence of IgG from patients with IDDM.

If this inhibition is the result of an antibody effect on GLUT-2 activity, it should also be manifest on the GLUT-2-transfected AtT20$_{ins}$ cell line but not on the GLUT-1-transfected cells. The expression of GLUT-2 in this cell line confers them with glucose transport characteristics remarkably similar to those found in islet cells. Purified IgG from the same patients with new-onset IDDM reduced the initial rate of glucose transport in GLUT-2-expressing AtT20$_{ins}$ cells from 15.5 mmoles 3-O-methyl-glucose/min/liter cell space to 6.2 mmoles 3-O-methyl-glucose/min/liter cell space, p<0.05, (FIG. 7A, FIG. 7B and FIG. 7C). This represents a 60% reduction in glucose transport in the presence of IgG from patients with IDDM compared to uptake in the presence of IgG from nondiabetic subjects.

Rat islet cells exhibit two kinetically distinct facilitated diffusion glucose transporter functions, a high $K_m$ function ascribed to GLUT-2 and a low $K_m$ transport function attributed to unidentified transporter. Results from a detailed kinetic analysis of the inhibition of glucose transport into islet cells induced by diabetic IgG indicated that the inhibition was directed against the high $K_m$ or GLUT-2 mediated function. As a test of the specificity of inhibition of GLUT-2, additional measurements in GLUT-1 expressing AtT20$_{ins}$ cells were made. Although nontransfected AtT20$_{ins}$ cells express GLUT-1 constituitively, the GLUT-1-transfected cell line overexpresses this protein and exhibits a greater than 10-fold increase in the velocity of glucose uptake which increases the accuracy of the transport measurement. Glucose uptake in GLUT-1-transfected AtT20$_{ins}$ cells treated with IgG from new-onset IDDM patients was indistinguishable from transport in the presence of IgG from nondiabetic individuals (FIG. 7A, FIG. 7B and FIG. 7C). These data indicate that IgG from new-onset IDDM patients does not inhibit glucose transport in AtT20$_{ins}$ cells that express a facilitative glucose transporter other than GLUT-2.

2. Specificity of Interactions of Sera from Patients with New-Onset IDDM and Nondiabetic Patients for GLUT-2-Expressing AtT20$_{ins}$ Cells It was important to establish the specificity of IgG binding to intact GLUT-2-expressing AtT20$_{ins}$ cells by performing analyses of IgG binding to the parent AtT20$_{ins}$ cells. Subtraction of the percentage of cells found in $R_2$ using the nontransfected AtT20$_{ins}$ cell line from the percentage of cells found in $R_2$ using the GLUT-2-expressing AtT20$_{ins}$ cell line would be expected to reflect the specific binding of IgG to GLUT-2. Such analyses were performed for each individual serum and a positive interaction was defined as an increase in IgG binding greater than two standard deviations from the mean observed in the nondiabetic patient population. It was found that 29 of 31 (94%) of the nondiabetic population were negative for IgG binding to GLUT-2 while 23 of 30 (77%) of sera from IDDM patients were positive (FIG. 8). Thus, 81% of negative results were from nondiabetic patients and 92% of positive results were from patients with IDDM (Table 2). The Youden index of these results gave J=0.73 (Table 2), and the level of significance of the separation between the two populations was p<0.0001.

TABLE 2

Regional Analysis of IgG Binding from Sera of Nondiabetic Children and Patients with IDDM to GLUT-2-Expressing AtT20$_{ins}$ Cells after Subtractions of IgG Binding to Nontransfected AtT20$_{ins}$ Cells.

| Patient Group | Individual with Peak Fluorescence in R$_2$ | |
|---|---|---|
| | >2 Standard Deviation* Shift | <2 Standard Deviation* Shift |
| IDDM | 23/30 (77%)† | 7/30 (23%)† |
| Nondiabetic | 2/31 (6%) | 29/31 (94%) |
| Sensitivity | 23/30 (77%) | |
| Specificity | 29/31 (94%) | |
| False Positive Rate | 2/25 (8%) | |
| False Negative Rate | 7/36 (19%) | |
| Youden Index: | J = 1 − (0.08 + 0.19) = 0.73 | |

*Defined as an increase in the peak number of fluorescent cells in R$_2$ fluorescence of greater than two standard deviations from the mean of the number of fluorescent cells in R$_2$ after treatment with sera from nondiabetic children.
†p < 0.0001 compared to the nondiabetic population

EXAMPLE IV

PERFUSION OF A COLUMN CONTAINING CGT-6 CELLS FOR INCREASED INSULIN PRODUCTION

A. Methods

Insulin secretion from CGT-6 (GLUT-2-expressing AtT-20$_{ins}$) cells was evaluated using a column perfusion technique (Knudsen et al., 1983). Cells were grown in liquid culture on microcarrier beads (InvitroGen). Approximately 50×10$^6$ cells were harvested by gentle centrifugation (500 rpm in a Sorvall RT6000B desk top centrifuge), resuspended in 4ml Krebs-Ringer salt (KRS) solution, pH 7.4, and loaded onto a Pharmacia P10/10 column. A cell count was obtained immediately before loading the column in the following manner. An aliquot of cells was taken, the beads digested with 1.2 U/ml Dispase (Boehringer Mannheim), the cell clumps were dispersed by extrusion through a 25 gauge needle and the cells were counted directly.

After the beads settled in the column, the top plunger of the column was gently inserted and the whole apparatus was submerged in a 37° C. water bath. The cells were then perifused as described below.

B. Results

In early secretion studies, a static incubation procedure was used in which cells were grown in tissue culture dishes and exposed to secretragogue-containing media over relatively long time periods (3 hours). While this technique was found to be valuable for screening new cell lines, it provides no information concerning the dynamics of insulin release. Perifusion experiments were therefore carried out to address this concern, and to evaluate whether glucose-stimulated insulin secretion from GLUT-2 expressing AtT-20$_{ins}$ cells occurs in a similar time frame as the rapid isl et β-cell response.

Native AtT-20$_{ins}$ cells, as well as GLUT-2 and GLUT-1 transfected lines were grown in liquid culture on microcarrier beads (InvitroGen), harvested into a Pharmacia P10/10 column, and washed with HBSS lacking glucose for 15 minutes. The capacity of lines CGT-6 (GLUT-2 transfected), CGT1-15 (GLUT-1 transfected) and the parental AtT-20$_{ins}$ cells to secrete insulin in response to glucose was compared (FIG. 9).

Perifusion with HBSS lacking glucose was continued after the 15 minute wash-out for an additional 25 minutes (FIG. 9, Phase 1). During this period, there was a gradual decline in insulin release from all three cell lines. Phase II was initiated by switching to HBSS buffer containing 5 mM glucose. A 10-fold increase in insulin release from CGT-6 cells was noted in the first sample, collected in the first 2.5 minutes after the switch to glucose-containing buffer (FIG. 9). This increase was sustained in 2 samples (representing a total of 5 minutes), after which insulin secretion declined to a second plateau that was 3-fold above the pre-glucose level. This biphasic pattern of insulin release is similar to that observed upon glucose stimulation of normal islets. Only small changes in insulin release were observed in phase II for either the parental AtT-20$_{ins}$ cells or the GLUT-1 transfected CGT1-15 line.

After 25 minutes of perifusion with 5 mM glucose, the cells were switched back to HBSS lacking glucose (FIG. 9, Phase III). Insulin secretion from the CGT-6 cells persisted at the glucose-stimulated level for approximately 10 minutes after the switch to buffer lacking glucose, but then declined rapidly. The low level of insulin release from parental AtT-20ins cells and CGT1-16 cells was further reduced during perifusion with glucose free media. In phase IV, cells were switched back to buffer containing 5 mM glucose. The CGT-6 cells again showed a much stronger secretory response to glucose, but the response was less rapid (requiring 15 minutes to reach maximum), and was without an obvious first phase and second phase.

Switching back to buffer lacking glucose in phase V again resulted in a dramatic albeit delayed reduction in insulin release from CGT-6 cells. In the last 25 minute phase (FIG. 9, phase VI), cells were perifused with HBSS containing the combination of 5 mM glucose and 0.5 μM forskolin. In keeping with the results from earlier static incubation experiments, GLUT-2 expressing CGT-6 cells exhibited a stronger insulin secretory response to glucose+forskolin than either the parental cells or the GLUT-1 transfected cells. The response of line CGT-6 to glucose+forskolin was sustained until the end of the experiment, suggesting that the cells were not depleted of insulin during the perifusion experiment. Consistent with this interpretation, no changes in insulin content were noticed in any of the cell lines isolated before and after perifusion experiments.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for or teach methodology, techniques and/or compositions employed herein.

Altman, et al. (1986), *Diabetes,* 35:625–633
Andersson, et al. (1989), *J. Biol. Chem.,* 264:8222–8229
Andreone, et al. (1989), *J. Biol. Chem.,* 264:363–369
Arora, et al. (1990), *J. Biol. Chem.,* 265:6481–6488
Ashcroft, S. J. H. (1980), *Diabetologia,* 18:5–15
Baekkeskov, et al. (1982), *Nature,* 298:167–169
Baekkeskov, et al. (1990), *Nature,* 347:151–156
Bell, et al. (1990), *Diabetes Care,* 13:198–208
Birnbaum, et al. (1987), *Science,* 235:1495–1498
Bright, G. M. (1987), *Diabetes,* 36:1183–1186
Canonico, P. L. (1989), *Endocrinology,* 125:1180–1186
Capecchi, M. R. (1989), *Trends in Genetics,* 5:70–76
Chen, et al. (1990), *Proc. Natl. Acad. Sci. U.S.A.,* 87:4088–4092
Clark, et al. (1990), *Endocrinology,* 127:2779–2788
Cockett, et al. (1990), *Bio/Technology,* 8:662–667.
Cone, et al. (1984), *Proc. Natl. Acad. Sci. U.S.A.,* 81:6349–6353
Danos, et al. (1988), *Proc. Natl. Acad. Sci. U.S.A.,* 85:6460–6464
DiMario, et al. (1988), *Diabetes,* 37:462–466
Doberson, et al. (1980), *N. Engl. J. Med.,* 303:1493–1498
Efrat, et al. (1988), *Proc. Natl. Acad. Sci. U.S.A.,* 85:9037–9041
Elias, et al. (1991), *Proc. Natl. Acad. Sci., U.S.A.,* 88:3088–3091
Flier, et al. (1987), *Science,* 235:1492–1495
Fritschy, et al. (1991), *Diabetes,* 40:37
Fukumoto, et al. (1988), *Proc. Natl. Acad Sci, U.S.A.,* 85:5434–5438
Gazdar, et al. (1980), *Proc. Natl. Acad. Sci. U.S.A.,* 77:2519–2523
Giroix, et al. (1984), *Biochem. J.,* 223:447–453
Giroix, et al. (1985), *Arch. Biochem. Biophys.,* 241:561–570
Gleichmann, et al. (1987), *Diabetes,* 36:578–584
Grandison, L. (1990), *Endocrinology,* 127:1786–1791
Halban, et al. (1983), *Biochem. J.,* 212:439–443
Hedeskov, C. J. (1980), *Physiol. Rev.,* 60:442–509
Hughes, et al. (1991), *J. Biol. Chem.,* 266:4521–4530
Irvine, et al. (1980), In: *Immunology of Diabetes,* Teviot Scientific Publications, pp. 117–154
Iynedjian, et al. (1989), *Proc. Natl. Acad. Sci. U.S.A.,* 86:7838–7842
Johnson, et al. (1990a), *J. Biol. Chem.,* 265:6548–6551
Johnson, et al. (1990b), *Science,* 250:546–549
Johnson, et al. (1990c), *N. Engl. J. Med.,* 322:653–659
Kuglin, et al. (1988), *Diabetes,* 37:130–132
Kuwajima, et al. (1986), *J. Biol. Chem.,* 261:8849–8853
Lacy, et al. (1986), *Ann. Rev. Med.,* 37:33–40
Lacy, et al. (1991) *Science,* 254:1782–1784
Lenzen, et al. (1987), *Acta Endocrinologica,* 115:514–520
Lernmark, et al., (1981), *Diabetology* 21:431–35
Lernmark, et al. (1982), *Diabetes Med.,* 4:285–292
Ludwig, et al. (1987), *Diabetes,* 36:420–425
Lynch, et al. (1991), *J. Cell Biol.,* 112:385–395
Maclaren, et al. (1975), *Lancet,* 1:997–1000
Madsen, et al. (1988), *Proc. Natl. Acad. Sci. U.S.A.,* 85:6652–6656
Magnuson, et al. (1989), *J. Biol. Chem.,* 264:15936–15942
Malaisse, et al. (1984), *Endocrinology,* 115:2015–2020
Malaisse, et al. (1990), *Biochem. Soc. Trans.,* 18:107–108
Mansour, et al. (1988), *Nature,* 336:348–352
Meglasson, et al. (1986), *Diabetes/Metabolism Rev.,* 2:163–214
Meglasson, et al. (1987), *Diabetes,* 36:477–484
Moore, et al. (1983), *Cell,* 35:531–538
Moriarity, C. M. (1978), *Life Sci.,* 23:185–189
Newgard, et al. (1986), *Proc. Natl. Acad. Sci. U.S.A.,* 83:8132–8136
Newgard, et al. (1990), *Biochem. Soc. Trans.,* 18:851–853
Nishi, et al. (1988), *Biochem. Biophys. Res. Comm.,* 157:937–943
O'Shea, et al. (1986), *Diabetes,* 35:943–946
Ora, et al. (1976), *Proc. Natl. Acad. Sci., U.S.A.* 73:1338–42
Orci, et al. (1989), *Science,* 245:295–297
Orci, et al. (1990), *Proc. Natl. Acad. Sci. U.S.A.,* 87:9953–9957
Permutt, et al. (1989), *Proc. Natl. Acad. Sci. U.S.A.,* 86:8688–8692
Praz, et al. (1983), *Biochem. J.,* 210:345–352
Prentki, et al.(1987), *Physiol. Rev.,* 67:1185–1248
Rossini, et al. (1985), *Ann. Rev. Immunol.,* 3:289–320
Sambrook, et al. (1989), *Molecular Cloning: A Laboratory Manual,* Cold Spring Harbor Press, pp. 16.30–16.55
Sarkar, et al. (1988), *Proc. Natl. Acad. Sci. U.S.A.,* 85:5463–5467
Sato, et al. (1962), *Proc. Natl. Acad. Sci. U.S.A.,* 48:1184–1190
Schwab, et al. (1989), *Proc. Natl. Acad. Sci. U.S.A.,* 86:2563–2567
Shimizu, et al. (1988a), *Diabetes,* 37:563–568
Shimizu, et al. (1988b), *Diabetes,* 37:1524–1530
Srikanta, et al. (1983), *N. Engl. Jrnl. Med.,* 308:322–25
Srikanta, et al. (1986), *Diabetes,* 25:139–142
Stoller, et al. (1989), *J. Biol. Chem.,* 264:6922–6928
Stossel, T. (1987), in *The Molecular Basis of Blood Diseases,* Chapter 14, pp. 499–533, W. B. Saunders Co. Philadelphia, Pa.
Sullivan, et al. (1991) *Science,* 252:718–721
Tal, et al. (1990), *J. Clin. Invest.,* 86:986–992
Thorens, et al. (1988), *Cell,* 55:281–290
Thorens, et al. (1990a), *Diabetes Care,* 13:209–218
Thorens, et al. (1990b), *Proc. Natl. Acad. Sci. U.S.A.,* 87:6492–6496
Trus, et al. (1981), *Diabetes,* 30:911–922
Turk, et al. (1987), *Prog. Lipid Res.,* 26:125–181
Ullrich & Wollheim, (1984), *J. Biol. Chem.,* 259:4111–4115
Vera, et al. (1989), *Mol. Cell Biol.,* 9:4287–4295
Vischer, et al. (1987), *Biochem. J.,* 241:249–255
Walder, J. (1988), *Genes & Development,* 2:502–504
Weinhouse, S. (1976), *Curr. Top. Cell. Regul.,* 11:1–50
Wilson, J. E. (1984), *Regulation of Carbohydrate Metabolism,* ed., Beitner, R. (CRC, Boca Raton, Fla.), pp. 45–85
Zheng, et al. (1990), *Nature,* 344:170–173

---

I claim:

1. A method for producing human insulin, the method comprising:
    (a) obtaining a cell that secretes human insulin in response to glucose, the cell comprising a hexokinase IV gene, an insulin gene and a GLUT-2 gene, wherein at least one of said genes is a recombinant gene introduced into the cell by means of a recombinant vector;
    (b) growing said cell in culture;
    (c) contacting said cell with a glucose-containing buffer for a period sufficient to allow said cell to respond;
    (d) collecting the media that has been in contact with said cell; and
    (e) purifying human insulin from the collected media.

2. The method of claim 1, wherein the cell is grown in contact with a solid support.

3. The method of claim 2, wherein the solid support used is gelatin beads.

4. The method of claim 2, wherein the cell is contained within a column.

5. The method of claim 1, wherein at least a portion of the insulin produced is encoded by a recombinant insulin gene.

6. The method of claim 1, wherein the buffer contains 5 mM glucose.

7. The method of claim 1, wherein the GLUT-2 gene is a recombinant gene.

8. The method of claim 7, wherein the GLUT-2 gene comprises a rat islet GLUT-2 gene.

9. The method of claim 7, wherein the recombinant GLUT-2 gene comprises a cDNA gene.

10. The method of claim 1, wherein the cell is further defined as a cell derived from a cell capable of forming secretory granules.

11. The method of claim 10, wherein the cell is further defined as a cell derived from an endocrine cell.

12. The method of claim 11, wherein the cell is further defined as a cell derived from a pituitary or thyroid cell.

13. The method of claim 12, wherein the cell is further defined as a cell derived from AtT-20 cells.

14. The method of claim 10, wherein the cell is further defined as a cell derived from GH-1 or GH-3 cells.

15. The method of claim 10, wherein the cell is further defined as a cell derived from a β cell.

16. The method of claim 15, wherein the cell is further defined as a cell derived from βTC, RIN or HIT cells.

17. The method of claim 1, wherein the cell expresses recombinant glucokinase.

18. The method of claim 17, wherein the cell comprises a recombinant glucokinase cDNA gene.

19. The method of claim 1, wherein the cell is further defined as having a reduced hexokinase activity relative to the cell line from which it was prepared.

20. The method of claim 13, wherein the cell is further defined as a CTG-5 or a CTG-6 cell.

21. The method of claim 20, wherein the cell is further defined as a CTG-6 cell.

22. A method for producing human insulin, the method comprising:
    (a) obtaining a population of cells that secrete human insulin in response to glucose, said cells containing at least about 1 mUnit of human insulin per million cells and comprising an insulin gene and a GLUT-2 gene, wherein at least one of said genes is a recombinant gene introduced into the cell by means of a recombinant vector;
    (b) growing said cells in culture;
    (c) contacting said cells with a glucose-containing buffer for a period sufficient to allow said cells to respond;
    (d) collecting the media that has been in contact with said cells; and
    (e) purifying human insulin from the collected media.

23. A method for producing human insulin, the method comprising:
    (a) obtaining a population of cells that secrete human insulin in response to glucose, the cells comprising an insulin gene and a GLUT-2 gene, wherein at least one of said genes is a recombinant gene introduced into the cell by means of a recombinant vector;
    (b) growing said cells in culture;
    (c) contacting said cells with a glucose-containing buffer for a period sufficient to allow said cells to respond;
    (d) collecting the media that has been in contact with said cells, said media containing at least about 5 Units of human insulin per liter of media; and
    (e) purifying human insulin from the collected media.

24. The method of claim 22, wherein said cells further comprise a recombinant hexokinase IV gene.

25. The method of claim 23, wherein said cells further comprise a recombinant hexokinase IV gene.

* * * * *

UNITED STATES PATENT AND TRADEMARK OFFICE
CERTIFICATE OF CORRECTION

PATENT NO. : 5,811,266
DATED : September 22, 1998
INVENTOR(S) : Christopher B. Newgard It is certified that error appears in the above-identified patent and that said Letters Patent is hereby corrected as shown below:

Title Page, item [60], line 2, delete "Jun. 20" and insert --Jun. 02-- therefor.

Signed and Sealed this

Twenty-ninth Day of December, 1998

*Attest:*

BRUCE LEHMAN

*Attesting Officer*  *Commissioner of Patents and Trademarks*